United States Patent
Wang et al.

(10) Patent No.: US 11,564,801 B2
(45) Date of Patent: Jan. 31, 2023

(54) PARTIALLY POROUS TIBIAL COMPONENT

(71) Applicant: Howmedica Osteonics Corp., Mahwah, NJ (US)

(72) Inventors: Aiguo Wang, Wayne, NJ (US); Matthew P. Poggie, Montclair, NJ (US); Nicholas Nai Guang Dong, Little Falls, NJ (US)

(73) Assignee: Howmedica Osteonics Corp., Mahwah, NJ (US)

( * ) Notice: Subject to any disclaimer, the term of this patent is extended or adjusted under 35 U.S.C. 154(b) by 247 days.

(21) Appl. No.: 16/429,807

(22) Filed: Jun. 3, 2019

(65) Prior Publication Data

US 2019/0314160 A1 Oct. 17, 2019

Related U.S. Application Data

(63) Continuation of application No. 15/923,517, filed on Mar. 16, 2018, now abandoned, which is a
(Continued)

(51) Int. Cl.
*A61F 2/38* (2006.01)
*A61F 2/30* (2006.01)
*A61F 2/46* (2006.01)

(52) U.S. Cl.
CPC .......... *A61F 2/389* (2013.01); *A61F 2/30767* (2013.01); *A61F 2/30907* (2013.01);
(Continued)

(58) Field of Classification Search
CPC ........ A61F 2/38; A61F 2/3836; A61F 2/3868; A61F 2/3886; A61F 2/389;
(Continued)

(56) References Cited

U.S. PATENT DOCUMENTS

| 3,064,645 | A | * | 11/1962 | Ficat .................. A61F 2/3601 123/23 |
| 3,605,123 | A | | 9/1971 | Pratt et al. |
| 3,808,606 | A | | 5/1974 | Tronzo |
| 3,855,638 | A | | 12/1974 | Pilliar |
| 3,906,550 | A | | 9/1975 | Rostoker et al. |

(Continued)

FOREIGN PATENT DOCUMENTS

| EP | 0761242 A1 | 3/1997 |
| JP | 2001087292 A | 4/2001 |
| WO | 02/17820 A1 | 3/2002 |
| WO | 2011056422 A1 | 5/2011 |

OTHER PUBLICATIONS

Extended European Search Report for Application No. EP14158287 dated Jun. 4, 2014.
(Continued)

*Primary Examiner* — Marcia L Watkins
(74) *Attorney, Agent, or Firm* — Lerner, David, Littenberg, Krumholz & Mentlik, LLP

(57) ABSTRACT

A method for removing a stem portion of an orthopedic implant from a bone comprises exposing an implanted orthopedic implant having a body portion, a stem portion interconnected to the body and a porous metal section forming an interconnection between the body and the stem portion. A cutting tool is mounted on a holder connected to an exposed surface of the orthopedic implant. The porous section is aligned with the cutting tool mounted on the holder. The entire porous section is cut by moving the cutting tool therethrough in a direction transverse to the stem portion axis. The implant body portion is then removed and then the stem portion is removed from the bone. The cutting tool may be a saw or chisel which may be mounted on a guide fixed to the body portion.

20 Claims, 15 Drawing Sheets

Related U.S. Application Data continuation of application No. 13/788,442, filed on Mar. 7, 2013, now Pat. No. 9,949,837.

(52) U.S. Cl.
CPC .......... *A61F 2/3877* (2013.01); *A61F 2/461* (2013.01); *A61F 2/3094* (2013.01); *A61F 2/30749* (2013.01); *A61F 2002/30011* (2013.01); *A61F 2002/3092* (2013.01); *A61F 2002/3093* (2013.01); *A61F 2002/3097* (2013.01); *A61F 2002/30179* (2013.01); *A61F 2002/30322* (2013.01); *A61F 2002/30451* (2013.01); *A61F 2002/30878* (2013.01); *A61F 2002/30879* (2013.01); *A61F 2002/30884* (2013.01); *A61F 2002/30891* (2013.01); *A61F 2002/30892* (2013.01); *A61F 2002/4619* (2013.01); *A61F 2002/4641* (2013.01)

(58) Field of Classification Search
CPC .......... A61F 2002/30172; A61F 2002/30179; A61F 2002/30749; A61F 2002/30879; A61F 2002/30884; A61F 2002/30891
See application file for complete search history.

(56) References Cited

U.S. PATENT DOCUMENTS

| | | |
|---|---|---|
| 4,000,525 A | 1/1977 | Klawitter et al. |
| 4,073,999 A | 2/1978 | Bryan et al. |
| 4,156,943 A | 6/1979 | Collier |
| 4,179,485 A | 12/1979 | Tritten |
| 4,355,428 A | 10/1982 | Deloison et al. |
| 4,479,271 A | 10/1984 | Bolesky et al. |
| 4,501,031 A | 2/1985 | McDaniel et al. |
| 4,550,448 A | 11/1985 | Kenna |
| 4,644,942 A | 2/1987 | Sump |
| 4,743,261 A | 5/1988 | Epinette |
| 4,759,767 A | 7/1988 | Lacey |
| 4,808,186 A | 2/1989 | Smith |
| 4,851,008 A | 7/1989 | Johnson |
| 4,865,603 A | 9/1989 | Noiles |
| 4,874,155 A | 10/1989 | Goul |
| 4,883,488 A | 11/1989 | Bloebaum et al. |
| 4,911,720 A | 3/1990 | Collier |
| 4,938,769 A | 7/1990 | Shaw |
| 4,944,756 A | 7/1990 | Kenna |
| 4,969,907 A | 11/1990 | Koch et al. |
| 4,986,834 A | 1/1991 | Smith et al. |
| 4,997,445 A | 3/1991 | Hodorek |
| 5,002,575 A | 3/1991 | Johnson |
| 5,019,103 A | 5/1991 | Van Zile et al. |
| 5,019,104 A | 5/1991 | Whiteside et al. |
| 5,034,186 A | 7/1991 | Shimamune et al. |
| 5,080,674 A | 1/1992 | Jacobs et al. |
| 5,108,434 A | 4/1992 | Ahrens et al. |
| 5,176,710 A | 1/1993 | Hahn et al. |
| 5,192,324 A | 3/1993 | Kenna |
| 5,222,983 A | 6/1993 | Schmitz et al. |
| 5,246,530 A | 9/1993 | Bugle et al. |
| 5,258,030 A | 11/1993 | Wolfarth et al. |
| 5,263,986 A | 11/1993 | Noiles et al. |
| 5,336,265 A | 8/1994 | Serbousek et al. |
| 5,358,533 A | 10/1994 | Noiles et al. |
| 5,370,698 A | 12/1994 | Heimke et al. |
| 5,397,359 A | 3/1995 | Mittelmeier et al. |
| 5,405,389 A | 4/1995 | Conta et al. |
| 5,413,605 A | 5/1995 | Ashby et al. |
| 5,441,537 A | 8/1995 | Kenna |
| 5,466,631 A | 11/1995 | Ichikawa et al. |
| 5,480,443 A | 1/1996 | Elias |
| 5,480,444 A | 1/1996 | Incavo et al. |
| 5,480,445 A | 1/1996 | Burkinshaw |
| 5,487,933 A | 1/1996 | White |
| 5,489,306 A | 2/1996 | Gorski |
| 5,504,300 A | 4/1996 | Devanathan et al. |
| 5,507,815 A | 4/1996 | Wagner et al. |
| 5,521,087 A | 5/1996 | Lee et al. |
| 5,534,027 A | 7/1996 | Hodorek |
| 5,571,203 A * | 11/1996 | Masini ............... A61F 2/30739 623/22.46 |
| 5,580,353 A | 12/1996 | Mendes et al. |
| 5,607,480 A | 3/1997 | Beaty |
| 5,609,641 A | 3/1997 | Johnson et al. |
| 5,645,593 A | 7/1997 | Woods et al. |
| 5,658,334 A | 8/1997 | Caldarise et al. |
| 5,658,352 A | 8/1997 | Draenert |
| 5,665,118 A | 9/1997 | LaSalle et al. |
| 5,672,284 A | 9/1997 | Devanathan et al. |
| 5,687,788 A | 11/1997 | Caldarise et al. |
| 5,700,688 A | 12/1997 | Lee et al. |
| 5,702,459 A | 12/1997 | Hummer et al. |
| 5,713,410 A | 2/1998 | LaSalle et al. |
| 5,716,412 A | 2/1998 | DeCarlo, Jr. et al. |
| 5,725,594 A | 3/1998 | McTighe et al. |
| 5,725,603 A | 3/1998 | Audousset et al. |
| 5,728,159 A | 3/1998 | Stroever et al. |
| 5,824,098 A | 10/1998 | Stein |
| 5,824,103 A | 10/1998 | Williams |
| 5,826,586 A | 10/1998 | Mishra et al. |
| 5,830,215 A | 11/1998 | Incavo et al. |
| 5,897,592 A | 4/1999 | Caldarise et al. |
| 5,989,472 A | 11/1999 | Ashby et al. |
| 6,005,164 A | 12/1999 | Johansson et al. |
| 6,008,430 A | 12/1999 | White |
| 6,008,431 A | 12/1999 | Caldarise et al. |
| 6,008,432 A | 12/1999 | Taylor |
| 6,010,336 A | 1/2000 | Shimotoso et al. |
| 6,022,509 A | 2/2000 | Matthews et al. |
| 6,060,640 A | 5/2000 | Pauley et al. |
| 6,087,553 A | 7/2000 | Cohen et al. |
| 6,139,581 A | 10/2000 | Engh et al. |
| 6,149,689 A | 11/2000 | Grundei |
| 6,179,876 B1 | 1/2001 | Stamper et al. |
| 6,193,761 B1 | 2/2001 | Treacy |
| 6,203,576 B1 | 3/2001 | Afriat et al. |
| 6,228,091 B1 | 5/2001 | Lombardo et al. |
| 6,280,478 B1 | 8/2001 | Richter et al. |
| 6,391,059 B1 | 5/2002 | Lemperle et al. |
| 6,520,964 B2 | 2/2003 | Tallarida et al. |
| 6,554,867 B1 | 4/2003 | Joos |
| 6,565,575 B2 | 5/2003 | Lewis |
| 6,582,470 B1 | 6/2003 | Lee et al. |
| 6,592,622 B1 | 7/2003 | Ferguson |
| 6,599,322 B1 | 7/2003 | Amrich et al. |
| 6,616,696 B1 | 9/2003 | Merchant |
| 6,652,588 B2 | 11/2003 | Hayes, Jr. et al. |
| 6,679,917 B2 | 1/2004 | Ek |
| 6,740,092 B2 | 5/2004 | Lombardo et al. |
| 6,797,006 B2 | 9/2004 | Hodorek |
| 6,800,094 B2 | 10/2004 | Burkinshaw |
| 6,855,150 B1 | 2/2005 | Linehan |
| 6,905,513 B1 | 6/2005 | Metzger |
| 6,913,623 B1 | 7/2005 | Zhu |
| 6,974,481 B1 | 12/2005 | Carson |
| 7,001,394 B2 | 2/2006 | Gundlapalli et al. |
| 7,001,672 B2 | 2/2006 | Justin et al. |
| 7,018,418 B2 | 3/2006 | Amrich et al. |
| 7,070,623 B2 | 7/2006 | Hunter et al. |
| 7,189,262 B2 | 3/2007 | Hayes, Jr. et al. |
| 7,241,313 B2 | 7/2007 | Unwin et al. |
| 7,255,715 B2 | 8/2007 | Metzger |
| 7,258,810 B2 | 8/2007 | Hunter et al. |
| 7,291,169 B2 | 11/2007 | Hodorek |
| 7,320,709 B2 | 1/2008 | Felt et al. |
| 7,357,817 B2 | 4/2008 | D'Alessio, II |
| 7,387,846 B2 | 6/2008 | Redepenning |
| 7,393,342 B2 | 7/2008 | Henniges et al. |
| 7,431,734 B2 | 10/2008 | Danoff et al. |
| 7,507,256 B2 | 3/2009 | Heck et al. |
| 7,513,912 B2 | 4/2009 | Hayes, Jr. et al. |
| 7,537,664 B2 | 5/2009 | O'Neill et al. |
| 7,544,209 B2 | 6/2009 | Lotke |

(56) References Cited

U.S. PATENT DOCUMENTS

| | | |
|---|---|---|
| 7,578,850 B2 | 8/2009 | Kuczynski et al. |
| 7,582,117 B2 | 9/2009 | Hunter et al. |
| 7,582,118 B2 | 9/2009 | Brown et al. |
| 7,597,715 B2 | 10/2009 | Brown et al. |
| 7,713,307 B1 | 5/2010 | Hall et al. |
| 7,771,483 B2 | 8/2010 | Justin et al. |
| 7,829,433 B2 | 11/2010 | Yamazaki |
| 7,833,274 B2 | 11/2010 | Popoola et al. |
| 7,842,093 B2 | 11/2010 | Peters et al. |
| 7,896,922 B2 | 3/2011 | Engh et al. |
| 7,896,923 B2 | 3/2011 | Blackwell et al. |
| 7,927,336 B2 | 4/2011 | Rasmussen |
| 7,988,736 B2 | 8/2011 | May et al. |
| 8,206,450 B2 | 6/2012 | Henry et al. |
| 8,317,871 B2 * | 11/2012 | Stone ............... A61F 2/4003 623/22.17 |
| 8,403,994 B2 | 3/2013 | Maloney et al. |
| 8,454,705 B2 | 6/2013 | Pressacco et al. |
| 8,556,972 B2 | 10/2013 | Gordon et al. |
| 8,828,311 B2 | 9/2014 | Medina et al. |
| 8,936,645 B1 * | 1/2015 | Masson ............ A61B 17/1753 623/19.11 |
| 9,237,950 B2 | 1/2016 | Hensley et al. |
| 9,636,229 B2 | 5/2017 | Lang et al. |
| 9,801,974 B2 | 10/2017 | Landon |
| 10,034,756 B2 | 7/2018 | Landon |
| 10,231,840 B2 | 3/2019 | Servidio |
| D856,518 S | 8/2019 | Dacus |
| 10,779,951 B2 * | 9/2020 | Kemp ............... A61F 2/4003 |
| D905,246 S | 12/2020 | Irwin et al. |
| 2001/0011190 A1 | 8/2001 | Park |
| 2002/0102857 A1 | 8/2002 | Sato |
| 2002/0153348 A1 | 10/2002 | Say et al. |
| 2002/0161448 A1 | 10/2002 | Hayes, Jr. et al. |
| 2002/0183845 A1 | 12/2002 | Mansmann |
| 2003/0028254 A1 | 2/2003 | Hunter et al. |
| 2003/0033020 A1 | 2/2003 | Hunter et al. |
| 2003/0045941 A1 | 3/2003 | Lewallen |
| 2003/0065401 A1 | 4/2003 | Amrich et al. |
| 2003/0083751 A1 | 5/2003 | Tornier |
| 2003/0120346 A1 | 6/2003 | Mercinek et al. |
| 2003/0135282 A1 | 7/2003 | Anitua |
| 2003/0171820 A1 | 9/2003 | Wilshaw et al. |
| 2003/0176921 A1 | 9/2003 | Lawson |
| 2003/0181984 A1 | 9/2003 | Abendschein |
| 2003/0220696 A1 | 11/2003 | Levine et al. |
| 2004/0133283 A1 | 7/2004 | Shetty |
| 2004/0143337 A1 | 7/2004 | Burkinshaw |
| 2004/0143338 A1 | 7/2004 | Burkinshaw et al. |
| 2004/0148026 A1 | 7/2004 | Bonutti |
| 2004/0162619 A1 | 8/2004 | Blaylock et al. |
| 2004/0167633 A1 | 8/2004 | Wen et al. |
| 2004/0199250 A1 | 10/2004 | Fell |
| 2004/0236424 A1 * | 11/2004 | Berez ............... A61B 34/20 623/908 |
| 2004/0243237 A1 | 12/2004 | Unwin et al. |
| 2004/0260396 A1 | 12/2004 | Ferree et al. |
| 2004/0267371 A1 | 12/2004 | Hayes et al. |
| 2005/0015153 A1 | 1/2005 | Goble et al. |
| 2005/0084407 A1 | 4/2005 | Myrick |
| 2005/0112397 A1 | 5/2005 | Rolfe et al. |
| 2005/0123672 A1 | 6/2005 | Justin et al. |
| 2005/0125068 A1 | 6/2005 | Hozack et al. |
| 2005/0177242 A1 | 8/2005 | Lotke |
| 2005/0196934 A1 | 9/2005 | Tazoe et al. |
| 2006/0004466 A1 | 1/2006 | Glocker et al. |
| 2006/0052875 A1 | 3/2006 | Bernero et al. |
| 2006/0116682 A1 | 6/2006 | Longo |
| 2006/0122708 A1 | 6/2006 | Nakamura et al. |
| 2006/0142869 A1 | 6/2006 | Gross |
| 2006/0147332 A1 | 7/2006 | Jones et al. |
| 2006/0149391 A1 | 7/2006 | Opie et al. |
| 2006/0161263 A1 | 7/2006 | Sul |
| 2006/0229715 A1 | 10/2006 | Istephanous et al. |
| 2007/0065779 A1 | 3/2007 | Mangano |
| 2007/0100461 A1 | 5/2007 | Incavo et al. |
| 2007/0129808 A1 | 6/2007 | Justin et al. |
| 2007/0142914 A1 | 6/2007 | Jones et al. |
| 2007/0179607 A1 | 8/2007 | Hodorek et al. |
| 2007/0203582 A1 | 8/2007 | Campbell |
| 2007/0255412 A1 | 11/2007 | Hajaj et al. |
| 2007/0287027 A1 | 12/2007 | Justin et al. |
| 2007/0288021 A1 | 12/2007 | Rickels et al. |
| 2007/0299528 A9 | 12/2007 | Lotke |
| 2008/0004709 A1 | 1/2008 | O'Neill et al. |
| 2008/0021566 A1 | 1/2008 | Peters et al. |
| 2008/0081007 A1 | 4/2008 | Steele et al. |
| 2008/0119941 A1 | 5/2008 | Seo et al. |
| 2008/0133020 A1 | 6/2008 | Blackwell et al. |
| 2008/0183291 A1 | 7/2008 | Scheller et al. |
| 2008/0188942 A1 | 8/2008 | Brown et al. |
| 2008/0269893 A1 | 10/2008 | Bhatnagar et al. |
| 2009/0048660 A1 | 2/2009 | Adden |
| 2009/0084491 A1 * | 4/2009 | Uthgenannt ............ A61L 27/34 156/153 |
| 2009/0093881 A1 | 4/2009 | Bandyopadhyay et al. |
| 2009/0187256 A1 | 7/2009 | Rauguth et al. |
| 2009/0228114 A1 | 9/2009 | Clark et al. |
| 2009/0265011 A1 * | 10/2009 | Mandell ............... A61F 2/38 623/20.15 |
| 2009/0265012 A1 | 10/2009 | Engh et al. |
| 2009/0270998 A1 | 10/2009 | Kokubo et al. |
| 2009/0292365 A1 | 11/2009 | Smith et al. |
| 2009/0326660 A1 | 12/2009 | Abendschein |
| 2009/0326671 A1 | 12/2009 | Schofield |
| 2009/0326674 A1 | 12/2009 | Liu et al. |
| 2010/0010638 A1 | 1/2010 | Jones et al. |
| 2010/0057211 A1 | 3/2010 | Cuckler et al. |
| 2010/0076501 A1 | 3/2010 | Hacking et al. |
| 2010/0076566 A1 | 3/2010 | Serafin, Jr. et al. |
| 2010/0100190 A1 | 4/2010 | May et al. |
| 2010/0100191 A1 | 4/2010 | May et al. |
| 2010/0131071 A1 | 5/2010 | O'Connor et al. |
| 2010/0179662 A1 | 7/2010 | Verne et al. |
| 2010/0256773 A1 | 10/2010 | Thijs et al. |
| 2010/0291286 A1 | 11/2010 | O'Neill et al. |
| 2010/0298947 A1 | 11/2010 | Unger |
| 2010/0305708 A1 | 12/2010 | Lang et al. |
| 2011/0004315 A1 | 1/2011 | Muratoglu et al. |
| 2011/0009974 A1 | 1/2011 | Blaylock et al. |
| 2011/0014081 A1 | 1/2011 | Jones et al. |
| 2011/0015749 A1 | 1/2011 | Engh et al. |
| 2011/0015750 A1 | 1/2011 | Popoola et al. |
| 2011/0022180 A1 | 1/2011 | Melkent et al. |
| 2011/0022181 A1 | 1/2011 | Kasahara et al. |
| 2011/0029092 A1 | 2/2011 | Deruntz et al. |
| 2011/0035018 A1 | 2/2011 | Deffenbaugh et al. |
| 2011/0071635 A1 | 3/2011 | Zhang et al. |
| 2011/0270404 A1 | 11/2011 | Khan et al. |
| 2012/0191200 A1 | 7/2012 | Choren |
| 2012/0253474 A1 | 10/2012 | Klein et al. |
| 2012/0296436 A1 * | 11/2012 | Klawitter ............ A61F 2/4003 623/19.14 |
| 2012/0330429 A1 * | 12/2012 | Axelson, Jr. ........ A61F 2/30771 623/20.19 |
| 2013/0006354 A1 | 1/2013 | Pressacco |
| 2013/0245777 A1 | 9/2013 | Jerry |
| 2014/0039621 A1 | 2/2014 | Gordon et al. |
| 2018/0271668 A1 * | 9/2018 | Kemp ................ A61F 2/4612 |
| 2018/0296351 A1 | 10/2018 | Landon |
| 2018/0333267 A1 | 11/2018 | Landon |
| 2018/0344468 A1 | 12/2018 | Landon |
| 2018/0344469 A1 | 12/2018 | Landon |
| 2018/0353300 A1 | 12/2018 | Landon |

OTHER PUBLICATIONS

Petrovic, et al., "Additive Manufacturing Solutions for Improved Medical Implants", InBiomedicine, Mar. 2012, 36 pages.

* cited by examiner

PARTIALLY POROUS TIBIAL COMPONENT

CROSS-REFERENCE TO RELATED APPLICATIONS

The present application is a continuation of U.S. patent application Ser. No. 15/923,517, filed on Mar. 16, 2018, which is a continuation of U.S. patent application Ser. No. 13/788,442, filed on Mar. 7, 2013, now U.S. Pat. No. 9,949,837, the disclosures of which are hereby incorporated herein by reference.

BACKGROUND OF THE INVENTION

Current keel implant devices, such as tibial components, are solid with high stiffness are commonly associated with diaphyseal load transfer or stress shielding. This invention provides a porous section for allowing bone ingrowth and a reduced stiffness keel device for more anatomical load transfer. In addition, the porous section allows easier removal of the implant during revision procedure.

The present invention also relates to a device having two different porous surfaces attached directly or indirectly to one another and a method for forming the same. The two porous surfaces may be separated by a solid or fully dense (non-porous) layer.

The present application is particularly directed toward a method of forming porous or partially porous metallic structures having different porosities for bone ingrowth and soft tissue ingrowth or attachment. Porous structures may also be formed for polymer attachment.

One method of producing the different porous structures uses rapid prototyping to produce low density three-dimensional structures. This is useful in applications where porous and partially porous metallic structures, and more particularly metal porous structures with interconnective porosity are advantageous for use. In addition, composite structures of metal and porous ceramics or porous polymer can be used.

Many structures, especially in the medical arts, require two different surfaces, each adapted for their own purposes. Along this line, a structure may have a first surface which needs to be porous for tissue ingrowth and a second surface which could have porosity adapted to be a bearing surface. Those structures can be produced by Selective Laser Melting (SLM). See for example U.S. Patent Publication No. 2007/0142914, the disclosure of which is incorporated herein by reference. The field of free-form fabrication has seen many important recent advances in the fabrication of articles directly from computer-controlled databases. These advances, many of which are in the field of rapid prototyping of articles such as prototype parts and mold dies, have greatly reduced the time and expense required to fabricate articles, particularly in contrast to conventional machining processes in which a block of material, such as a metal, is machined according to the engineering drawings. One example of a modern rapid prototyping technology is the selective laser sintering process practiced by systems available from 3D Systems, Valencia, Calif. According to this technology, articles are produced in a layer-wise fashion, from a laser-fusible powder that is dispensed one layer at a time. The powder is fused, remelted or sintered, by the application of laser energy that is directed in raster-scan fashion to portions of the powder layer corresponding to a cross-section of the article. After fusing of the powder on one particular layer, an additional layer of powder is dispensed, and the process repeated with fusion taking place between the current layer and the previously laid layers, until the article is complete. In a first step of such process, a CAD file of an acetabular cup component is loaded into the Magics software package as a single part. The file may then be divided into three separate solid volumes having a 1.1 mm thick outer layer—this layer will be used to create the 80% porous bone ingrowth surface; 0.1 mm thick intermediate layer—this layer will be a fully dense layer that supports the bone ingrowth surface; and 0.8 mm thick inner layer—this will be used to create an interlock surface for a polymer injection molding. The three layers, when completed, will comprise the metal insert of the acetabular cup. Further, the first surface or portion may include different layers having different gradients of porosity. For example, the first surface may include an outer region having a porosity of approximately 80%. Moving more inwardly normal, with regard to the first surface, the porosity may alter such that the porosity is increased or in a preferred embodiment, the porosity decreases even until the porosity is almost zero. Of course, the present invention contemplates a situation where the porosity changes from position to position depending on the requirements of the device.

Cementless bone implant technologies provide a variety of porous surfaces that allows for bone ingrowth into the implant. This ingrowth allows for a better transfer of mechanical loads to the surrounding bone tissues and decreases bone resorption due to stress shielding. As with all primary implants sometimes a revision surgery is necessary to remove the implant. With non-cemented implants osseointegration blurs the bore/implant interface. This allows for the potential to lose large quantities of bone stock, when the implant is removed under conventional means. Other disadvantages of the current removal techniques include increased metal debris at and around the surgical site, increased heat and increased time in the operating room (OR). The proposed system addresses these issues and provides a method to remove porous material from cementless implants.

The porous material and manufacturing methods of the present invention can be used for other applications. One of the current concerns with modern total knee arthroplasty is the issue of femoral bone resorption due to stress shielding. This is most commonly found in the distal/anterior region behind the patellar groove of the implant. As femoral components are most commonly manufactured from Cobalt Chromium or titanium alloy, they have a significantly higher modulus of elasticity than the bone. Additionally, most femoral components are substantially rigid due to the amount of solid material that encompasses the space between the articular surface and the surfaces that mate with the resected femur. Bone remodels in the presence of load and in the natural knee, the articular surfaces are loaded by the patella and tibia. The replacement of that bearing with a stiff metal component shields the bone from much of the load in the anterior and posterior regions, leading to a lack of remodeling and ultimately, resorption. By making the femoral component essentially "hollow" and filling the space with foam, it becomes a more flexible component, which is better able to transfer the loads from the articular surfaces to the resected bone. This allows for remodeling of the bone in all regions and prevents stress shielding.

Current literature suggests several surgical methods to remove cementless implants during revision surgeries. These methods include the use of an oscillating cutting system such as oscillating saws and instruments which apply blunt striking force. Both methods have yielded positive effects, but present obvious disadvantages when used with solid implants.

Oscillating cutting systems are used to quickly cut up to the bone/implant interface and remove enough bone to allow the implant to be pulled from the bone. However, if the implant is not completely free, this results in large amounts of bone stock loss when the implant is extracted. With the oscillating system, when the blade reaches the porous coating of the otherwise solid implant, the high frequency motion can cause porous material to be dispersed throughout the surgical site. This may lead to subsequent revisions due to host response from debris particles or degradation of articulating surfaces due to body wear caused by the debris. Furthermore, friction between the blade and the implant can cause heat generation, in which the implant will act as a heat sink. The distribution of heat throughout the implant can transfer to the bone and cause bone tissue necrosis.

Blunt striking with an osteotome is also an effective means for separating the anchoring mechanisms of an implant from the planar force bearing surfaces. This allows access to the smaller anchoring point, which requires smaller, more precise tools to extract, or the surgeon can choose to leave them in. However, without a counter force, the bone provides the only resistance to implant movement. As such, the force from blunt striking may cause inadvertent damage to the bone surrounding the implant.

As used herein when referring to bones or other parts of the body, the term "proximal" means close to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body.

BRIEF SUMMARY OF THE INVENTION

A cementless bone fixation keel, extending from the metaphyseal seating surface of an orthopedic implant, such as a tibial implant, comprises a porous portion adjacent to the bone metaphyseal porous seating surface, and a solid portion extending to the diaphysis.

The extent of porosity of the keel portion can be adjusted to achieve a desired implant stiffness. The pore size of the porous portion is preferred in the range of 10 micron to 1000 micron, in which 100-400 micron is preferred for bone ingrowth application. The porosity is preferred between 40% to 80%. The porous portion of the keel can have either a surface porosity or a through-thickness porosity. The later will allow tissue to grow through the proximal porous portion of a tibial keeled implant.

The strength of the porous portion could be reinforced by inner high density elements such as a gradually decreasing porosity towards the center in the direction perpendicular to the surface of the keel or by means of near solid or totally solid reinforcing members or struts directionally oriented to best support applied loads.

The diaphyseal keel portion outer surface is closed off to prevent bone ingrowth but the stiffness of the construct can be reduced by inclusion of a lower density core structure. The inner lower density structure has a porosity of 10% to 80%. The solid outer surface could also contain struts that are directionally oriented to best reduce bending stiffness.

The total stiffness of the keel is preferred to be 20-80% less than that of a solid keel with the same material.

The bone fixation keel of the present invention is made from a bio-compatible material such as Ti, Ti alloy, or CoCr alloy.

The porous portion of the keel encourages the bony ingrowth for metaphyseal load transfer and the solid portion of the keel provides the device alignment and stability. A fully porous keel section also provides the surgeon full visibility of the implant/bone interface on x-ray inspection.

The porous keel section allows for an easier revision of the component since a tool can be provided to cut through the porous area.

One cementless implant removal tool described herein is a linear blunt force applicator that holds the implant and drives a cutting tool, such as a chisel, through the cementless material, i.e., bone and the porous metal. The cementless implant removal tool of the present invention allows for precise extraction of implants that lie on a single planar surface. One embodiment specifically applies to revision of novel implants described above which have a porous band of material integrated into a tibial baseplate and keel of a tibial implant. The removal device is comprised of an adapter that fits between the tibial baseplate holder and an impaction handle. Attached is a linear rod that supports a driving mechanism such as described by Goul (U.S. Pat. No. 4,874,155). The driving mechanism supports an adapter that holds a blade such as in a chisel.

One embodiment of the removal device is assembled by attaching the baseplate holder to the top of the baseplate. This may be accomplished by using the same system on the baseplate as is used to connect the bearing to the baseplate. The adapter is attached to the holder and the impactor handle attached to the adapter. The blade is attached to the adapter supported by the driving mechanism. Preferably the design allows the blade to be up to about 3 inches below the bottom of the baseplate. The device is operated by holding the tibial impactor handle and engaging the driving mechanism until it reaches the cancellous bone and implant interface. Once at the interface the cutting mechanism is driven through the porous baseplate keel material either by a power tool or manually. The adapter can preferably be rotated incrementally to −60 and 60 degree orientations and the device driven again through the remaining porous material. The baseplate will then be free from its anchoring points and able to be removed easily. The remaining keel may have a central threaded portion to allow for its removal.

Other embodiments include gauging and adjustment mechanisms to allow for offsets in any and all directions. Also other driving methods may be used, including ratcheting and motorized drivers. Also cutting may be achieved by different blades including flat, pointed, serrated and notched.

The present invention may provide a blunt cutting force as performed with the osteotome, but includes a counter force to prevent the implant from moving and potentially damaging the surrounding bone. The gauging and adjustment mechanisms provide a more precise execution of implant removal as well reproducibility of procedure. Though metal debris may be generated, the cutter may be designed with a lack of moving parts which help keep the debris localized. Also a stationary blade, such as a chisel, decrease friction and reduces heat generation.

Alternately an embodiment utilizing an oscillating saw can be used. The holder which attaches to the baseplate and to a saw can be identical to that described above with respect to a blunt force instrument. The holder preferably locks on the same undercut surfaces formed on the proximally facing side of the tibial baseplate used to lock the polyethylene bearing to the baseplate.

Another aspect of the invention is a semi-hollow, foam filled femoral component that has more flexibility than current solid femoral components. The semi-hollow femoral component replaces the articular surface of the distal femur. The device is comprised of a thin solid articular surface, which provides a bearing surface to articulate with a tibial bearing and a patellar component or the natural patella. Solid re-enforcing struts protrude from the non-bearing side of the thin solid articular surface and are shaped to transfer load from the resected femur to the articular surface. These struts may be added using SLM technology. The volume remaining between the reinforcing struts, the resected femur and the thin solid articular surface is filled with an engineered foam structure such as a urethane foam. The thin articular surface is of constant or variable thickness, sufficient to provide the strength needed to handle the stresses induced at the articular interface. The solid re-enforcing struts provide mechanical strength and some stiffness to the component in order to handle the loads transferred between the resected femur and the articular surface. The profile of the surface formed by the ends of these struts can match the geometry of existing resections of contemporary knee systems (typically five; planar cuts formed in the distal end of the femur) or can be customized to a unique geometry to match alternate methods of resecting the distal femur. The foam filler provides some additional mechanical strength to the component as well as provides a surface in direct opposition to the bone for either biological fixation or cement interdigitation.

In addition, in another aspect of the invention, a patella with porous surfaces may be manufactured using the material and methods of the present invention. The patella has three distinct layers produced entirely by the Selective Laser Melting (SLM) process to optimize the performance of the physical and mechanical properties of the component. The component is designed as a hybrid structure with a porous structure designed for bone ingrowth, an engineered structure designed for polyethylene interlock, and a fully dense structure that serves as barrier between the two porous structures. In addition, there is a fully dense core within each of the three patella pegs that provide additional mechanical strength to the structure. The porous layer designed to contact tissue and allow tissue ingrowth is approximately 1 mm thick. A 600 µm octahedral unit cell structure with 30 percent randomization is applied to replicate cancellous bone and provide optimal pore size and porosity for bone ingrowth. This structure has openings of 100-1000 µm in diameter with most recent measurements averaging 319 µm. The structure is 60-75% porous with most recent measurements averaging 68%. The porous layer designed for polymer interlock is designed to be under 1 mm thick. A 1000 µm octahedral unit cell structure is optimized for polymer molding operations. The polymeric material infiltrates the metallic grid and is stopped by the fully dense metal layer, preventing penetration into the tissue ingrowth layer. Likewise tissue cannot grow into the metallic grid. The fully dense intermediate layer is intended to separate the two porous layers preventing the polymer from penetrating the ingrowth layer during polymer molding operations. In addition, it provides structural support for the patella component to maintain dimensional stability. This layer is designed to be 381 µm thick. The peg portion of the patella component also features a fully dense region for structural and mechanical support. See WO 2011/056422 (PCT/US 2010/053314), the disclosure of which is incorporated herein by reference.

One aspect of the invention is a tibial implant comprising a solid metal baseplate having a bone contacting surface. A porous metal spacer section is fused to the bone contacting surface of the baseplate. A fully dense stem portion having an attachment area is also fused to the porous metal spacer section of the baseplate. The fully dense stem portion is spaced at least 2 mm from the baseplate bone contacting surface by the porous metal spacer section. The tibial implant porous metal spacer area and the fully dense stem portion may be in the form of a v-shaped keel. The porous metal spacer area and the fully dense stem portion may comprise a plurality of solid reinforcing struts extending through the 2 mm porous area. The porous metal spacer section has a pore size of 100 to 400 µm and preferably has pores formed by open polyhedron structures. The polyhedron is an preferably octahedron. The fully dense stem portion may surround a porous core so that only the outer layer of stem is fully dense.

Another aspect of the invention is a method for manufacturing the tibial baseplate implant, which includes providing a solid metal baseplate substrate and constructing a porous metal section on the metal baseplate substrate by layer by layer additive manufacturing using a laser (SLM). The substantially non-porous (fully dense) metal stem portion is constructed on the porous area by layer by layer additive manufacturing using a laser in a similar manner. The implant may be constructed in a manner where the porous area and the stem portion have a v-shape. A plurality of non-porous, i.e., solid struts may extend through the v-shaped porous area which struts can also be formed by SLM. The metal used is selected from the group consisting of Titanium, Titanium alloy and cobalt chrome molybdenum alloy.

Another aspect of the invention is a method for removing a stem portion with a porous area as described above of an already implanted orthopedic implant from a bone comprising exposing an implanted orthopedic implant having a body portion and a stem portion interconnected to the body. The stem portion extends along an axis into a bone canal and has a porous metal section forming an interconnection between the bone and the stem portion. A cutting tool is mounted on a holder connected to an exposed surface of the orthopedic implant. The porous section is aligned with the cutting tool mounted on the holder. The surgeon cuts through the entire porous section of the implant by moving the cutting tool therethrough in a direction transverse to the stem portion axis. The surgeon then removes the implant body portion and stem portion from the bone. The method may further comprise slidably mounting the cutting tool on a guide rail extending from the holder by mounting a first end of the guide rail on the holder connected to the body portion of the implant. The guide rail extends from the holder along an axis transverse to the axis of the stem portion. The cutting tool is moved along the rail into contact with the porous metal section to cut the stem portion from the body portion.

The method for removing the stem portion may further comprise slidably mounting a carriage on the rail, the carriage is coupled to the cutting tool and moving the carriage with a drive system towards the stem axis to perform the cutting operation. The drive system for moving the carriage may comprise a hand actuated clamp or may be electrically driven.

Another aspect of the invention is an instrument for separating a stem portion of an already implanted orthopedic implant from a body portion thereof. The orthopedic implant having a porous interface area between the stem and body portions. The instrument includes a rail having a first end and a second end. A coupling element at the first end of the rail is provided for coupling the rail to the body portion of the orthopedic implant. The rail extends in a direction transverse to a longitudinal axis of the stem. A carriage is mounted on the rail for movement along the rail from the second end to the first end. A cutting tool is mounted on the carriage and spaced from the rail along the stem axis and positioned to engage the porous interface section between the body portion and the stem portion of the orthopedic implant. A hand actuated drive system engaging the carriage is capable of moving the carriage towards the first end of the rail. The implant may be a tibial component and the stem portion is a v-shaped keel having a proximal portion connected to a distal facing surface of the tibial component by the porous interface section. The cutting tool may have a stop element thereon spaced toward the second end of the rail from a cutting edge of the cutting tool. The cutting tool may be a saw or a chisel. The v-shaped keel typically has a cylindrical central stem portions with medially and laterally extending wing portions having a relatively narrow thickness in the anterior-posterior direction of 2-6 mm.

Another aspect of the invention is a prosthetic femoral component for implantation on a prepared distal femur. The femoral component has a bearing element having an outer condylar surface for contesting a tibial bearing surface. The bearing element has an inner surface matching a shape of the outer condylar surface. A plurality of reinforced struts are formed on the inner surface of the bearing element and extend a distance therefrom. The struts have ends aligned in planes matching an anterior surface, a posterior surface, and a distal surface of a prepared distal femur. The struts form a plurality of voids therebetween, the voids stretching between the inner surface of the bearing and the ends of the struts. A polymeric foam is provided for filling the voids.

The bearing element of the femoral component is formed of sheet metal or other metal having a thickness less than 0.125 inches. The thickness of the metal between the outer condylar surface and the inner surface of the bearing element may vary or may be uniform. The struts are made by additive layers by selective laser melting (SLM) titanium powder.

The polymer foam is preferably made from urethane.

Another aspect of the invention is a patellar component and a method of making the prosthetic patellar component. The method includes forming a bone contacting first metal layer by selective laser melting. The first layer has openings of 100-1000 µm and 60-75% porous. A fully dense intermediate metal second layer is formed on the first layer. A polymer contacting third metal layer in the form of a porous grid is formed on the solid metal layer.

The method of making the patellar implant includes forming the fully dense layer with a plurality of solid pegs extending outwardly from a side the fully dense layer on which the bone contacting layer is formed. The pegs are received in bores formed in the remaining patella bone. Preferably the plurality of pegs are covered by the first metal layer. Ultrahigh molecular weight polyethylene is molded into the third porous grid metal layer to form the bearing surface. The polyethylene receiving grid openings are about 1000 µm. The third porous layer may have a convex outer surface such that a convex polyethylene bearing is formed.

As used herein when referring to bones or other parts of the body, the term "proximal" means close to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body.

DETAILED DESCRIPTION

Figure 1:
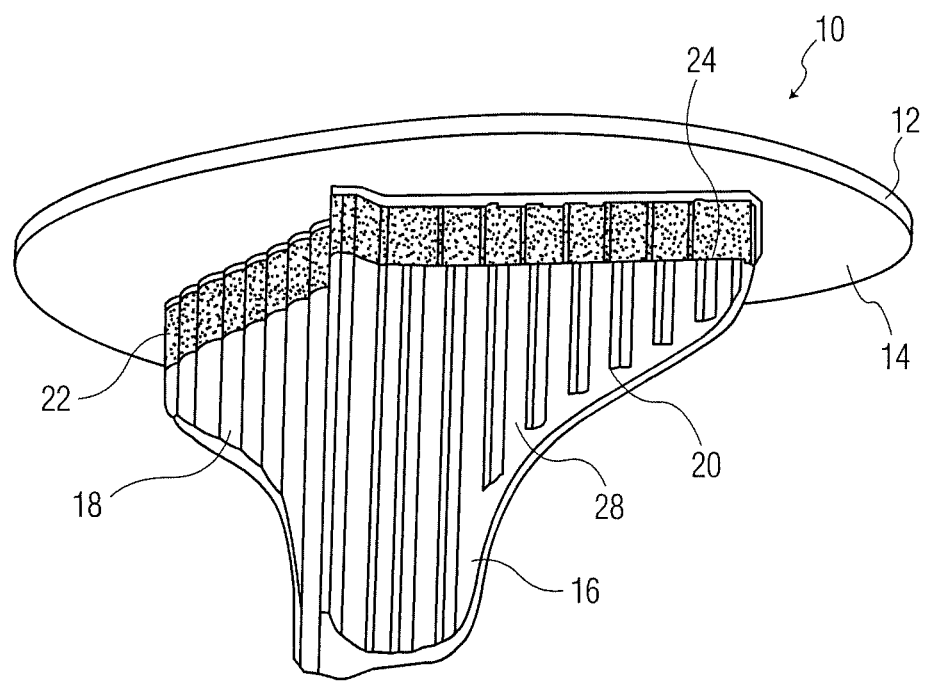
FIG. 1 is a perspective view of a tibial baseplate, including a porous area intermediate the bone contacting surface of the baseplate and a solid metal v-shaped keel.

Referring to FIG. 1, there is shown a perspective view of a tibial component generally denoted as 10, including a baseplate 12 with a bone contacting surface 14 and a proximally facing surface 15. A keel 16 extends distally from the bone contacting surface 14 of baseplate 12. Typically, keel 16 has a v-shape, including wings 18 and 20 on a medial and a lateral side of the tibial component 10. While a tibial component is shown other implants such as patellar implants and femoral implants could incorporate pegs or stems having porous cross-sections.

Plate 12 may be either solid or porous to allow bone ingrowth upon implantation of the tibial component bone connecting surface 14. As shown in FIG. 1, a porous area 22 extends distally from bone contacting surface 14. A porous area 22 is integrally formed on both bone contacting surface 14 and a proximal surface 24 of keel 16 below area 22. While baseplate 12 and keel 16 are preferably solid, they could be porous or, to improve implant stiffness, could have a solid outer surface surrounding a porous core to improve flexibility. Also shown in FIGS. 1 and 1A are outer scalloped surfaces 28 extending in a proximal-distal direction.

Figure 1A:
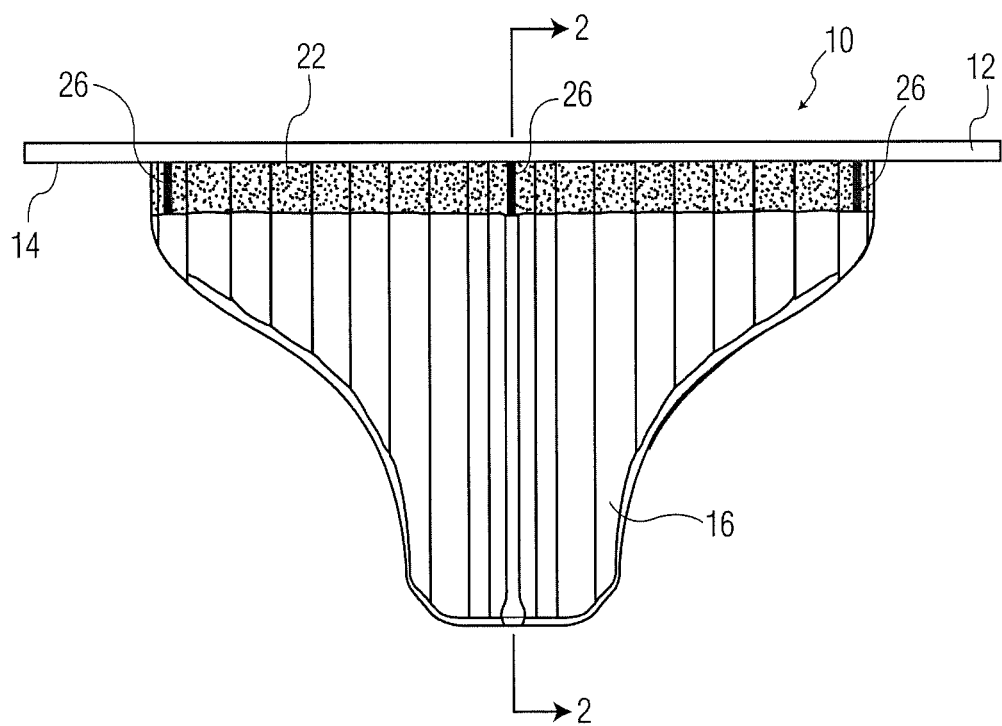
FIG. 1A is an elevation view of the tibial component of FIG. 1, including three solid struts extending through the porous area, the struts connecting the bone contacting surface and keel of the tibial baseplate.

Referring to FIG. 1A, there is shown an elevation view of a modified version of the tibial component 10 shown in FIG. 1. In this version, baseplate 12 and keel 16 are identical to that described above, however, porous area 22 is reinforced by three or more solid struts 26 extending from surface 24 to surface 14. Struts 26 add portional strength to the construct while, as will be described below, without hindering the ability to separate baseplate 12 from keel 16 during revision surgery. Struts 26 are shown located centrally and adjacent ends of wings 18 and 20 of keel 16. These struts are located to resist loads applied to implant 10 during use, which for a tibial implant is mainly in a proximal-distal direction.

Figure 2:
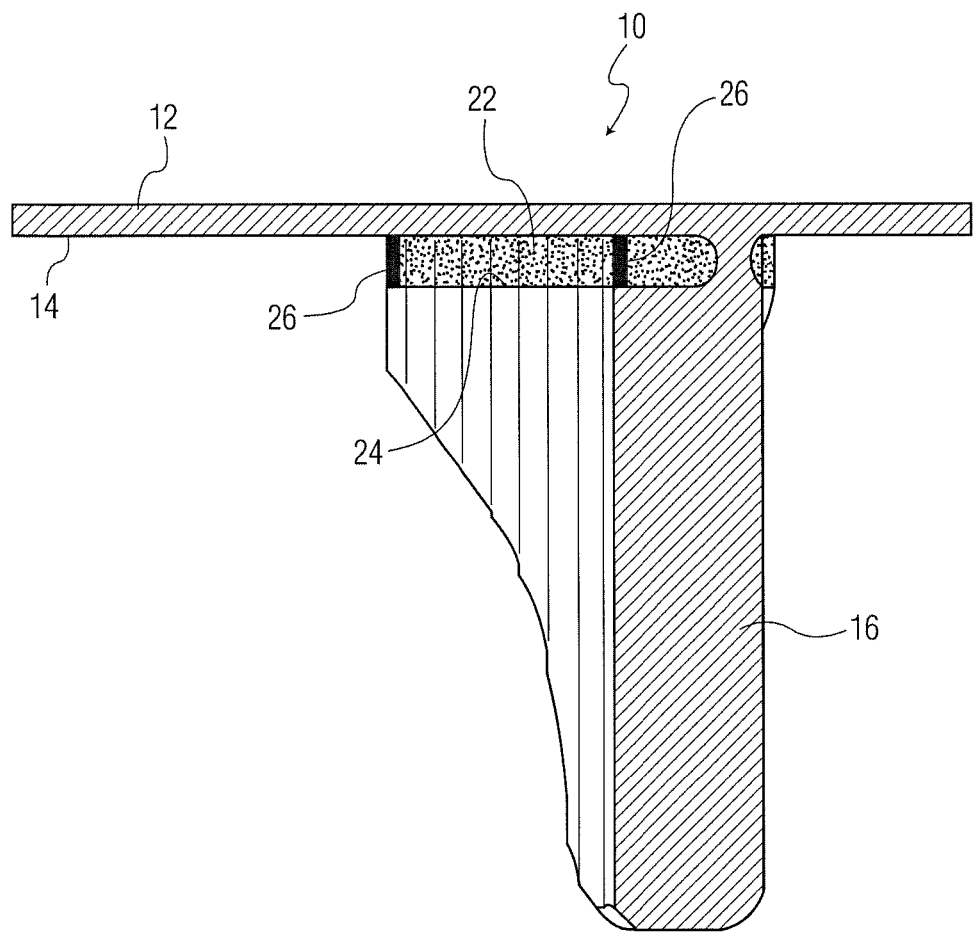
FIG. 2 is a cross-sectional view of the tibial component of FIG. 1 along lines 2-2 including the central solid strut shown in FIG. 1A.

Referring to FIG. 2, there is shown a cross-sectional view along lines 2-2 of FIG. 1A.

As shown, keel 16 and baseplate 12 have solid struts 26, which connect these two parts, two of which are shown in FIG. 2. Porous area or layer 22 is shown extending between top surface 24 of the solid portion of keel 16 to bottom bone contacting surface 14 of baseplate 12. It should be noted that tibial components typically include features formed on their proximally locking surfaces 15 for mounting a polyethylene bearing element, and these features have been omitted from FIGS. 1, 1A, and 2 for simplification. It should also be noted that while a v-shaped keel has been described, a circular or part circular stem can be coupled via the porous area 22 to baseplate 12. Such a stem would include a central solid strut or a plurality of struts extending from a bone contacting surface through the porous area 22 to provide extra strength for the tibial component 10. It can also be seen that the outer surface of keel 16 includes scalloped areas 28, which aid in resisting implant rotation but which could easily be eliminated rendering the keel outer surface planar.

Figure 3:
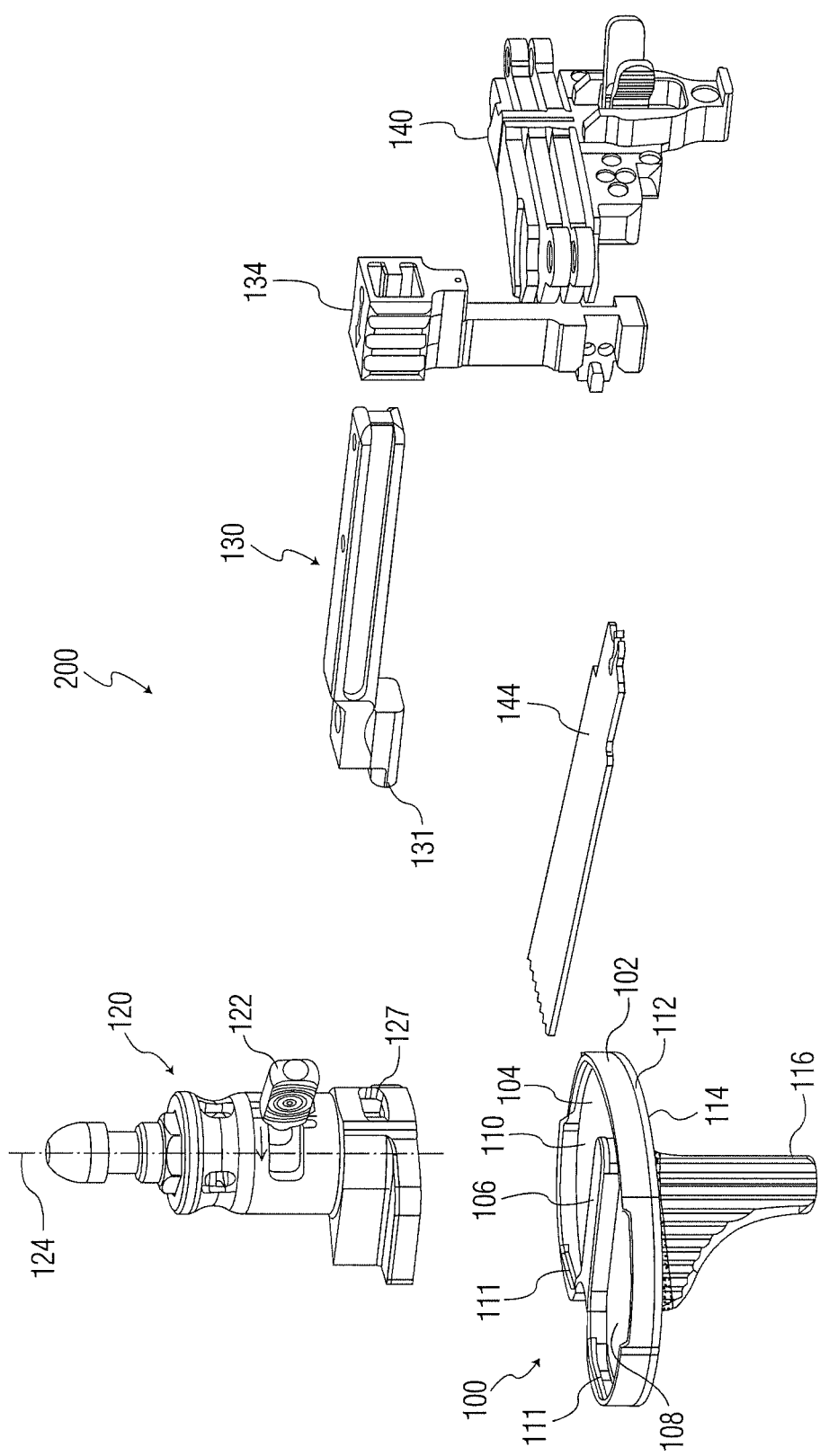
FIG. 3 is an exploded view of an instrument for separating the keel portion of the tibial component from the bone contacting surface of the baseplate by cutting through the porous area connecting the same with an oscillating.

Referring to FIG. 3, there is shown a first embodiment of an implant removal tool generally devoted as 200 for removing an already implanted tibial component 100 from the proximal tibia during revision surgery. As is typical, the proximal portion of implant 100 includes an outer peripheral wall 102 surrounding a proximally facing surface 104. As shown, a central intracondylar portion 106 separates condylar medial and lateral areas 108 and 110. Also shown are typical features 111 adapted to lock a polyethylene bearing component (not shown) to the tibial component 100. The baseplate portion 112 includes a bone contacting surface 114 and keel 116, which are identical to that shown in FIGS. 1-2. Also shown is an adapter or holder 120, which can be selectively mounted on proximally facing surface 104 of tibial component 100, preferably using the same locking elements 111 used to couple the polyethylene bearing component to the tibial component. Adapter or holder 120 includes a locking element 122, which can, in a first position, lock the adapter 120 to the tibial component 100 and in a second position allow for its removal. Also shown is a rail element 130, which has a tongue 131 which mounts on in an opening 127 in adapter or holder 120 and slidably receives a saw-guide mounting element 134, which can move in an anterior/posterior direction so that a slotted saw-blade guide 140 can be moved toward and away from the porous area between baseplate 112 and keel 116 (better seen in FIG. 5). If desired, element 130 can be rotatably mounted with respect to baseplate 100 so it may swing in a medial-lateral direction ±60 degrees around axis 124 of holder 120. A saw blade 144 is also shown, which blade can be mounted on any typical oscillating saw power unit. Typically slotted guide 140 can be slid up and down on a post 136 to vary the proximal-distal height of the slots.

Figure 4:
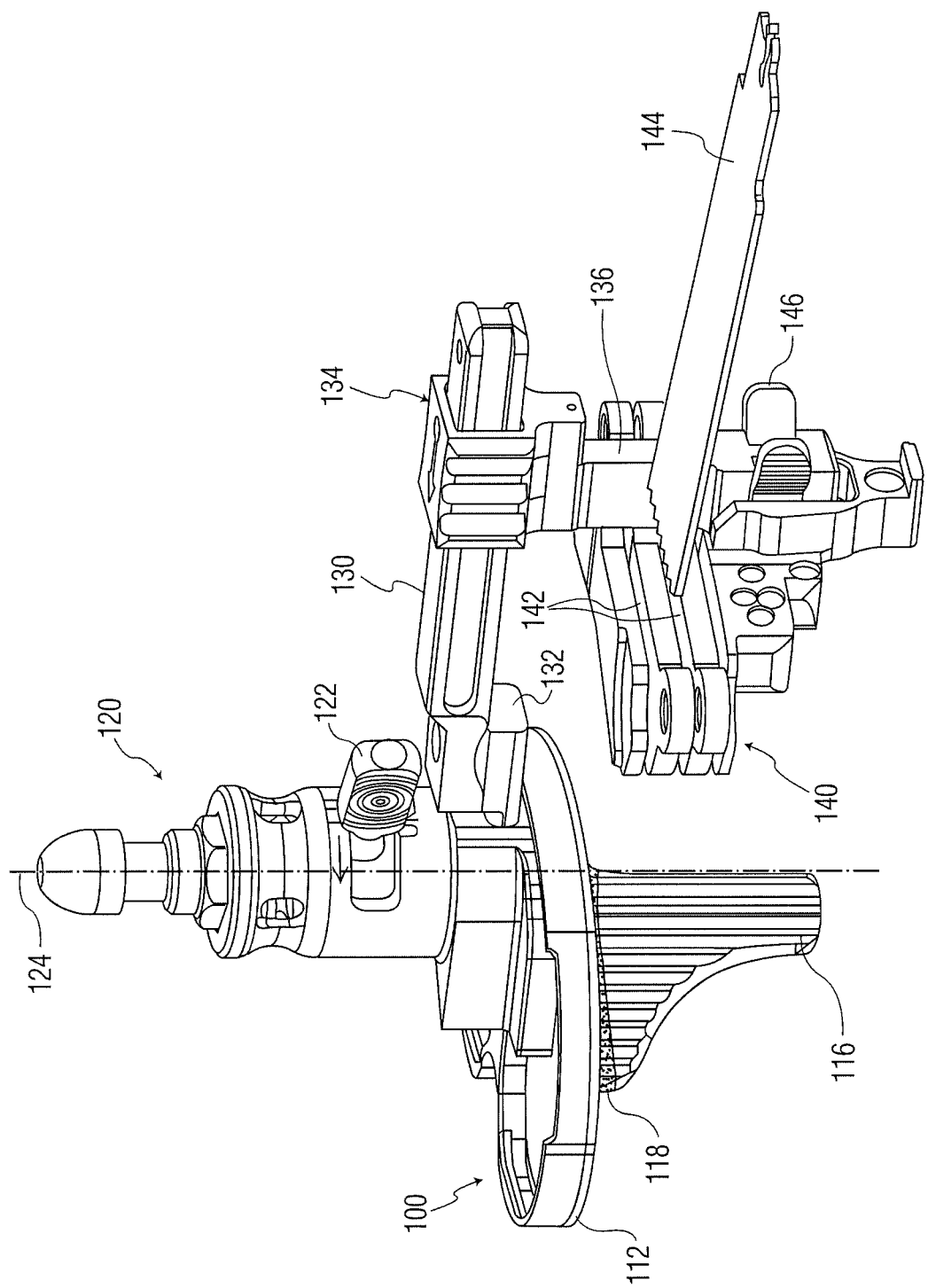
FIG. 4 shows the instrument of FIG. 3 assembled to the proximal surface of the tibial component, including an oscillating saw guide slot aligned with the porous area of the implant.
Figure 5:
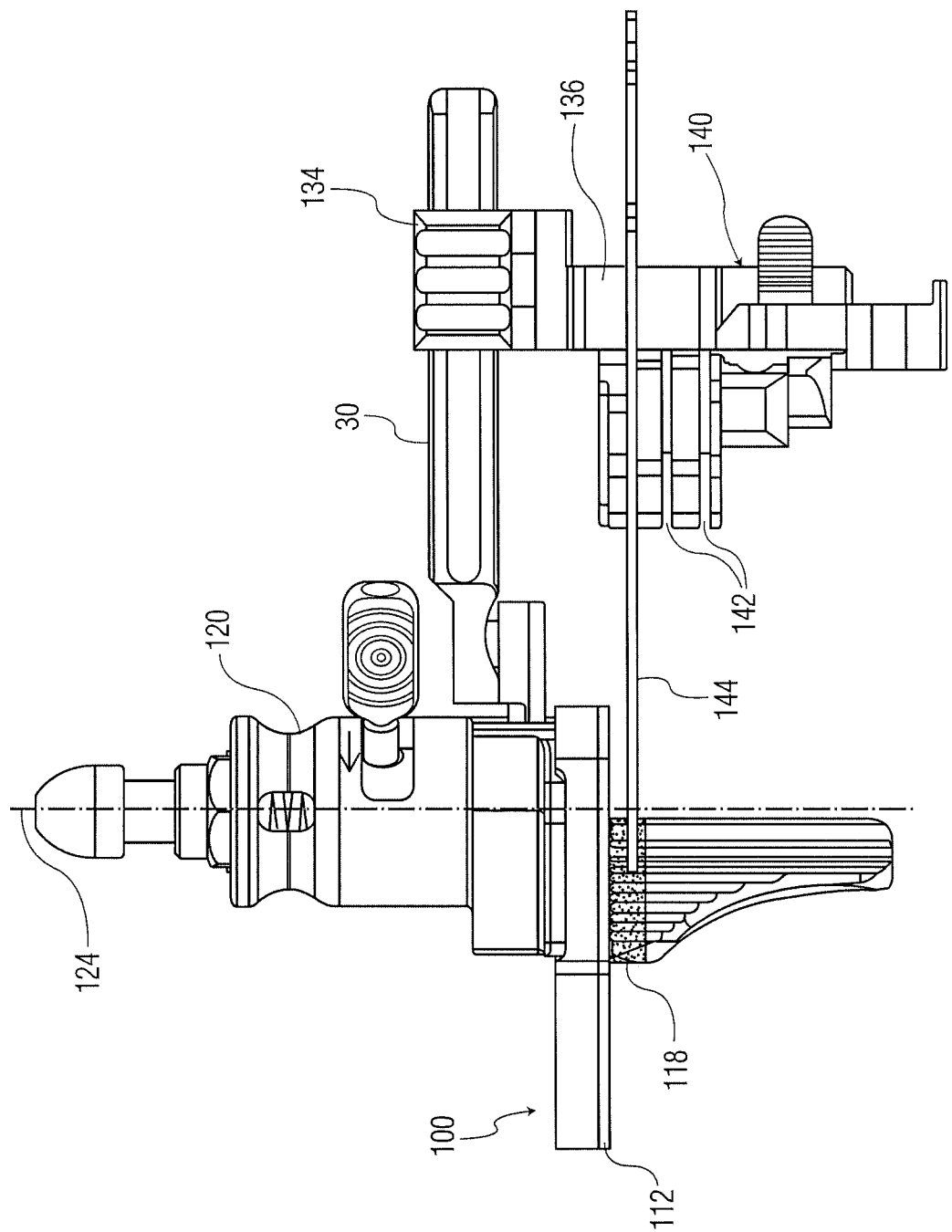
FIG. 5 is an elevation view of the assembled instrument of FIG. 4.

Referring to FIGS. 4 and 5, there is shown tibial component 100, adapter 120, rail 130, and saw guide 140 assembled to slidable mounting element 134 for guiding saw blade 144 into the porous area 118 of baseplate 100. Adapter or holder 120 is shown fixably mounted to central boss 106 of tibial baseplate 100 with locking element 122 in the lock position. Guide rail 130 has a leading end 132 mounted on actuator 120 such that slidable mounting element 134 can toward or away move cutting guide 140 toward and away from tibial component 100. Saw guide 140 includes a plurality of slots 142 for guiding saw blade 144 at different proximal-distal levels. Saw guide 140 may be moved in a proximal-distal direction along post 136 to properly align saw blade 144 with the porous area 118 of tibial component 100. The preferred embodiment a pair of spring elements 146 are used to selectively lock and release cutting guide 140 in the desired proximal-distal location along post 136. As indicated above, saw blade 144 can be driven by any electric or pneumatic oscillating saw drive system and can be moved along rail 130 and, if desired, rotated about axis 124 to be able to cut the entire porous areas 22, 118 connecting the keel 16, 116 to baseplate 12, 112. FIG. 5 is identical to FIG. 4 with the exception that oscillating saw blade 144 is now in contact with porous area 118 of tibial component 100.

Figure 6:
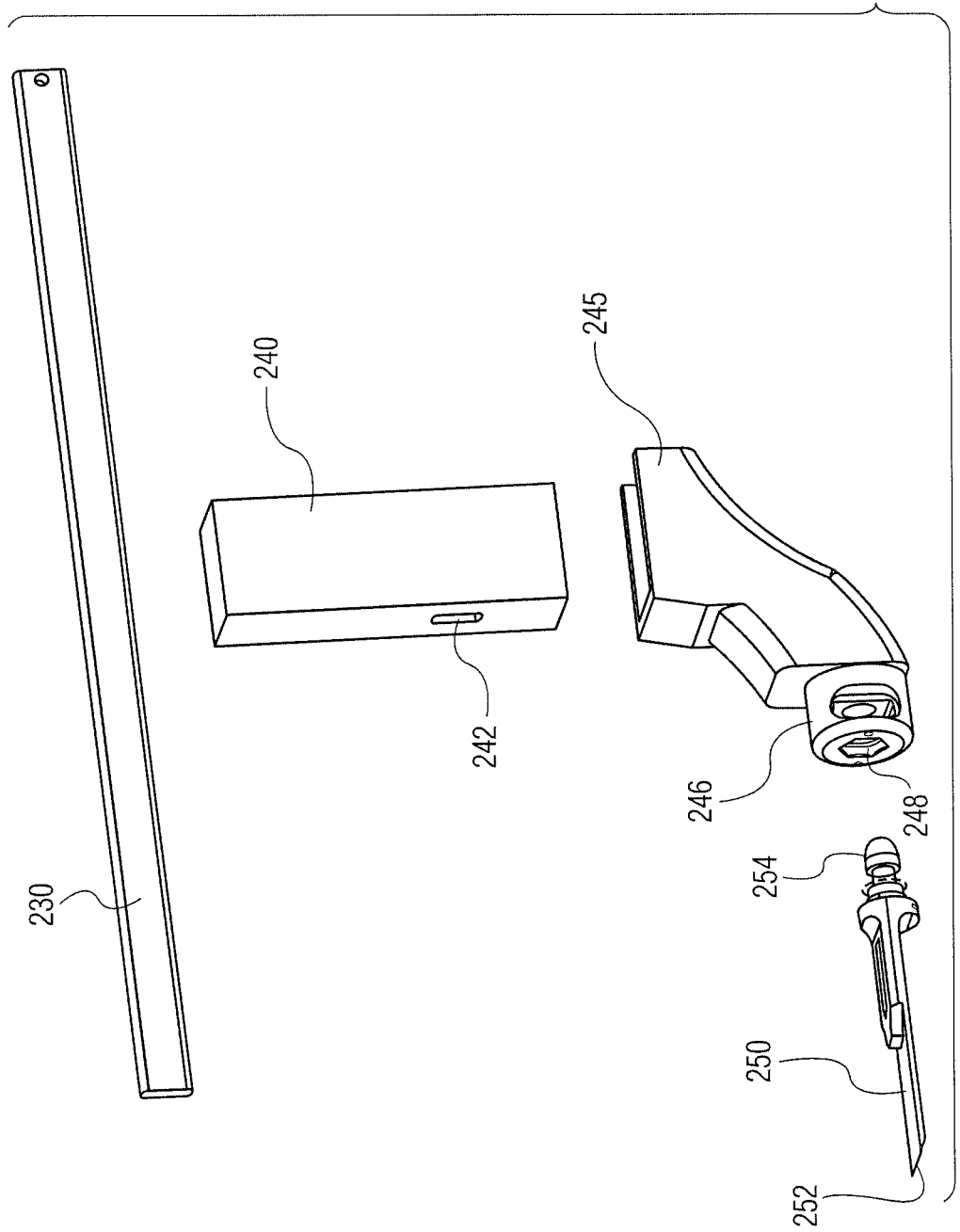
FIG. 6 shows an alternate embodiment of the instrument of FIG. 4 for separating the keel from the tibial baseplate using a chisel-like instrument.
Figure 7:
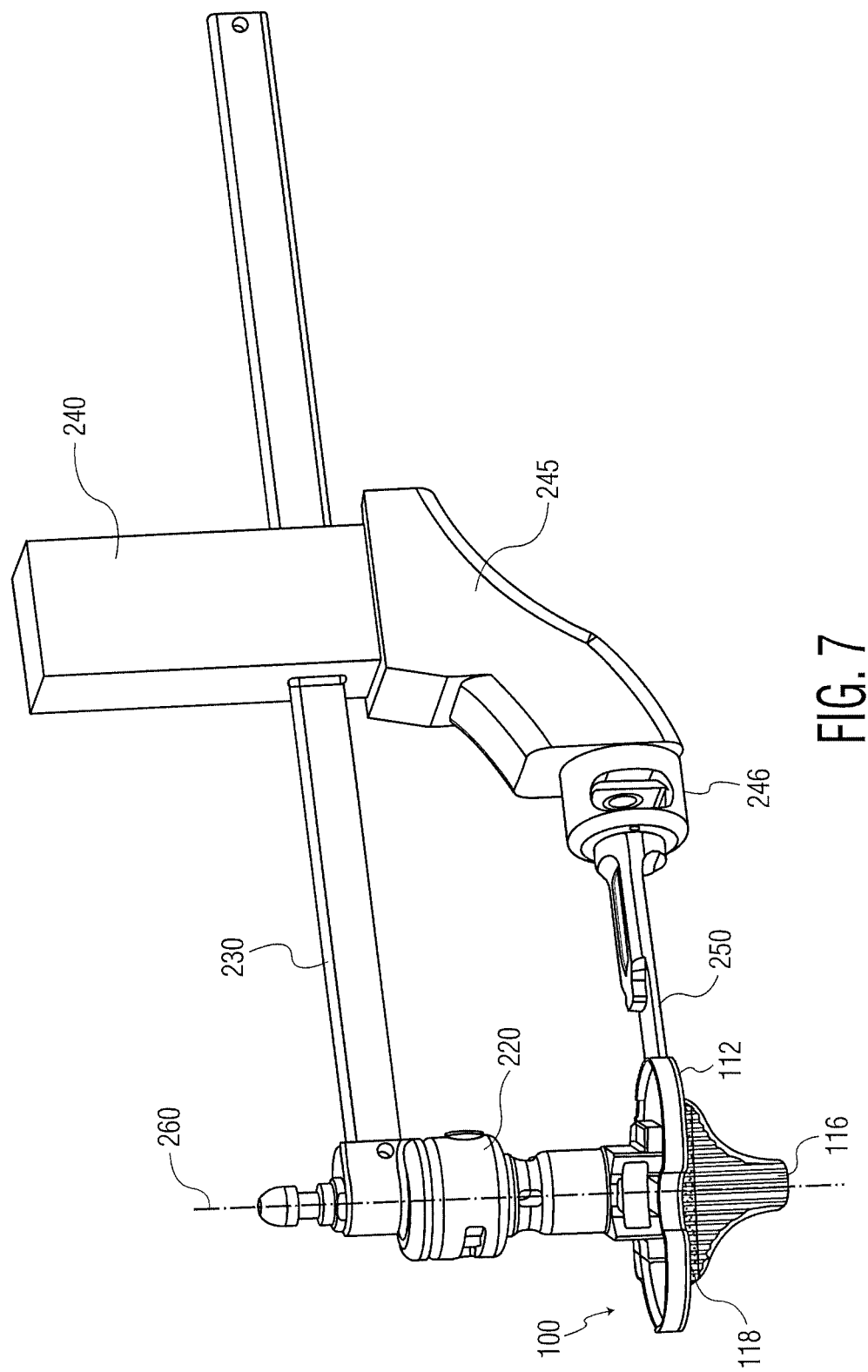
FIG. 7 is a perspective view of the instrument of FIG. 6 coupled to the proximal surface of a tibial component with the chisel-like instrument aligned with the porous area of the tibial component.
Figure 8:
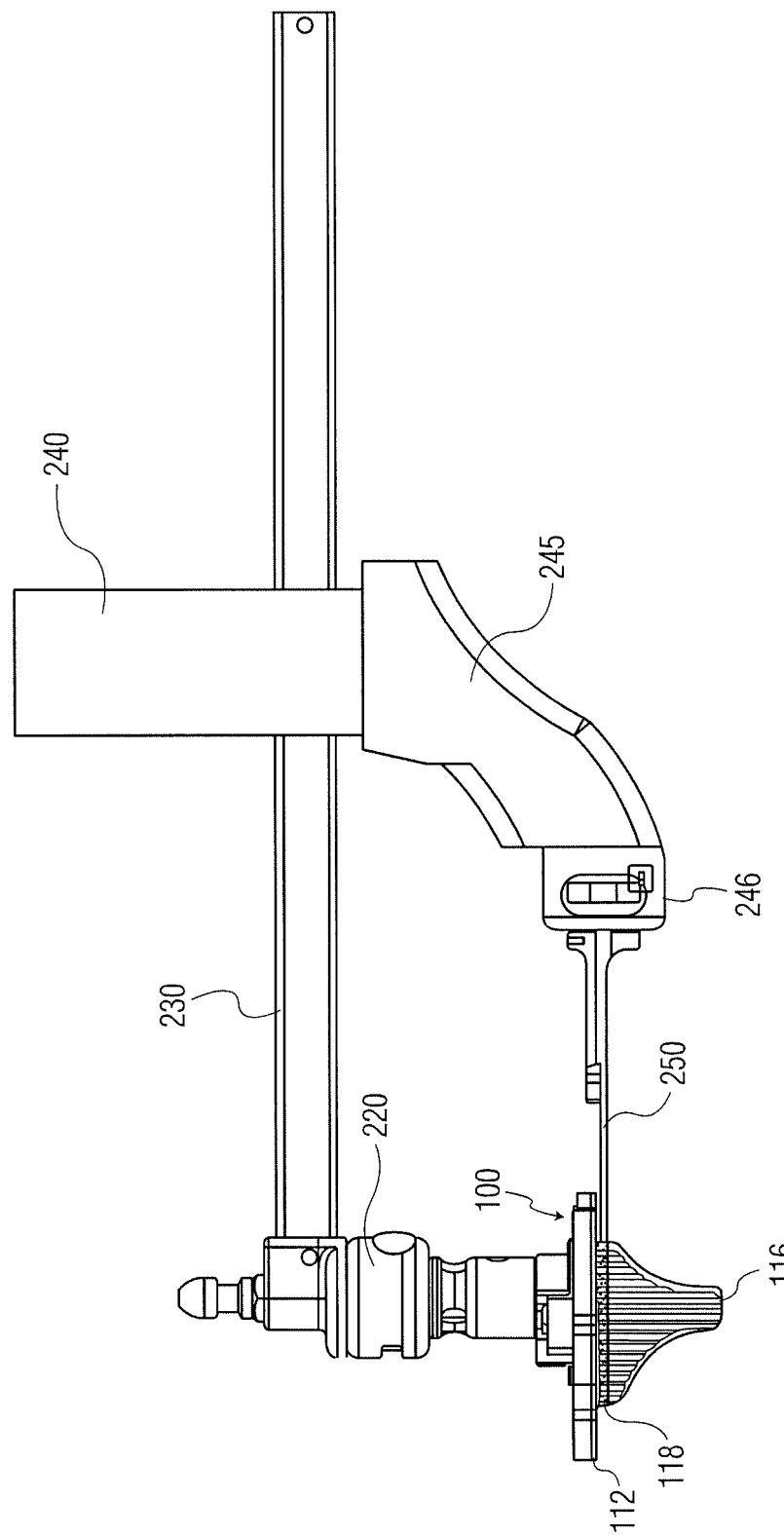
FIG. 8 is an elevation view similar to FIG. 7.

Referring to FIGS. 6 and 7, there is shown an alternate instrument for separating keel 116 from baseplate 112. In this system, an adapter 220 is mounted on tibial component 100 in a manner similar to that described above with regard to FIGS. 4 and 5 with a rail 230 extending therefrom. A guide element 240 is slidably mounted on rail 230 via a slotted opening 242 for movement toward and away from tibial component 100. Guide element 240 connects to an adapter 245, which adapter 245 in turn is slidably mounted on element 240 for movement in a proximal-distal direction. Adapter 245 has a mounting element 246 with a bore 246, which can releasably couple a chisel-like blade element 250 thereon via a coupling element 254. Sliding element 240 may be impacted such as by a hammer once tip 252 of blade 250 engages with porous area 118 of tibial component 100. In order to facilitate the separation of baseplate 112 from keel 116 through porous area 118, rail 230 may be rotated on adapter 220 about axis 260 so that chisel-like blade 250 can impact area 118 at any position between the medial and lateral ends of v-shaped keel 116. Normally, at least ±60° rotation about the sagittal plane is allowed by the structure. Thus, during use in revision surgery, the chisel-like blade can be advanced toward baseplate 100 as well as rotated with respect thereto about axis 260 thus allowing the surgeon to cut through porous area 118.

Figure 9:
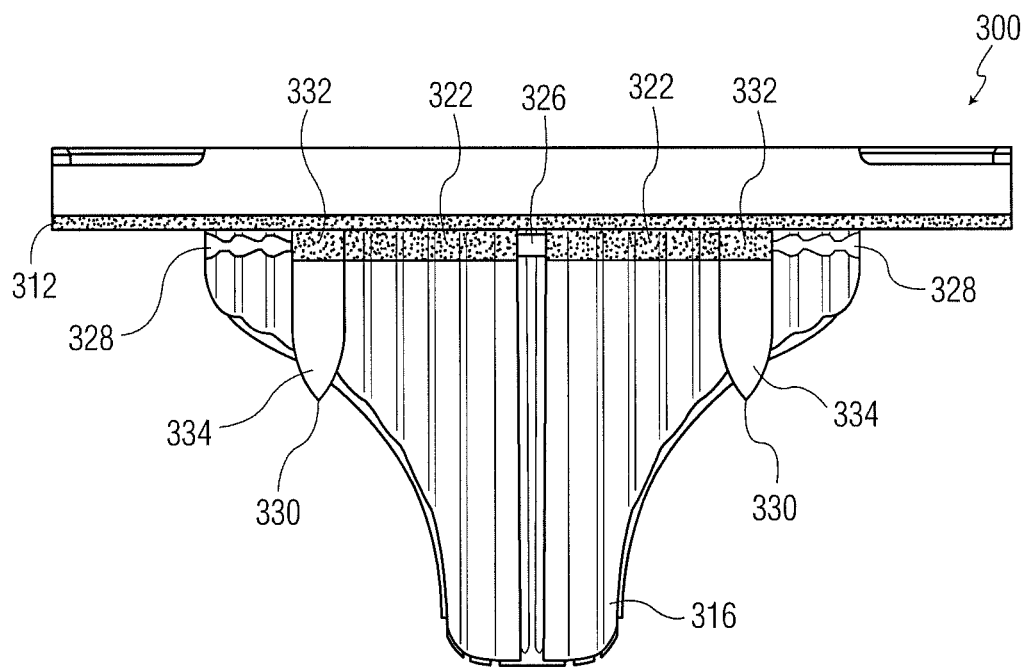
FIG. 9 shows an alternate tibial component, including the porous area between the tibial baseplate, the keel, and a plurality of spikes.
Figure 10:
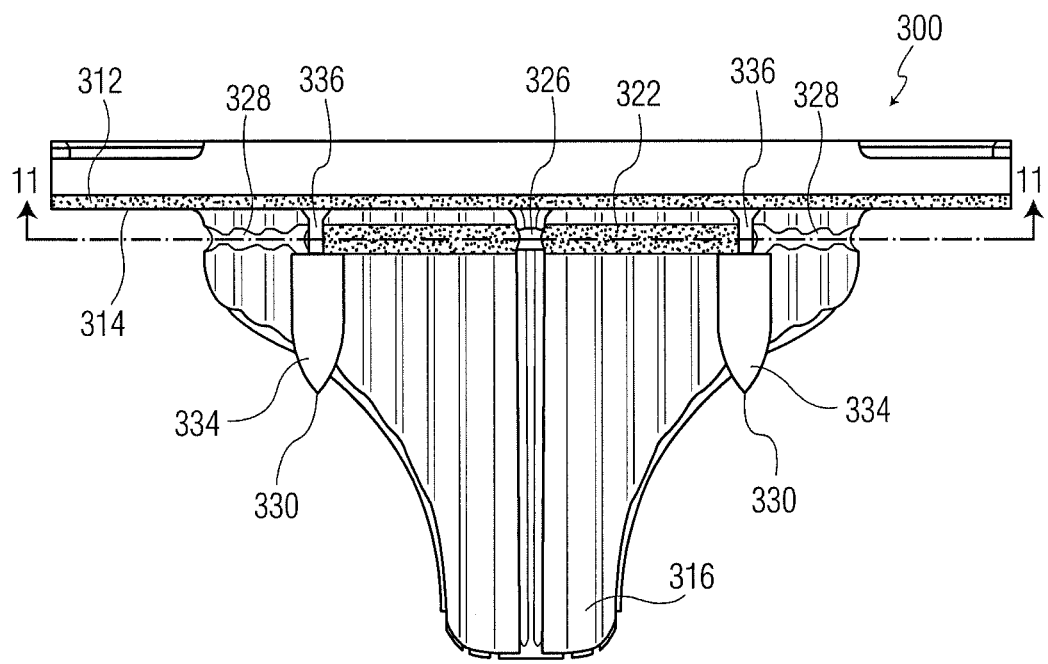
FIG. 10 shows the tibial component of FIG. 9 with the porous area removed to reveal solid reinforcing struts extending between the baseplate and the keel and through the spikes adapted to engage the proximal tibia.

Referring to FIGS. 9 and 10, there is shown an alternate tibial component 300 with a baseplate 312 having an optional distal porous baseplate area 314, a solid keel 316, and a porous area 322 toward keel 316 and area 312. Keel 316 is essentially the same as that described with regard to tibial component 10 and 100 as above. However, the tibial component 300 of FIGS. 9 and 10 include two or more spikes 330, which have a porous portion 332 and a solid tip portion 334. As shown in FIG. 10, the porous portions 332 of the spikes 330 can have a solid core 336 to reinforce the connection of the spikes 330 to baseplate 312. If baseplate 312 has a partially porous area 314, the solid extension portions would extend therethrough to solid portions of the tibial baseplate 312. As with tibial component 10, tibial component 300 can have a central solid strut 326 and solid areas 328 further connecting keel 316 to baseplate 312.

Figure 11:
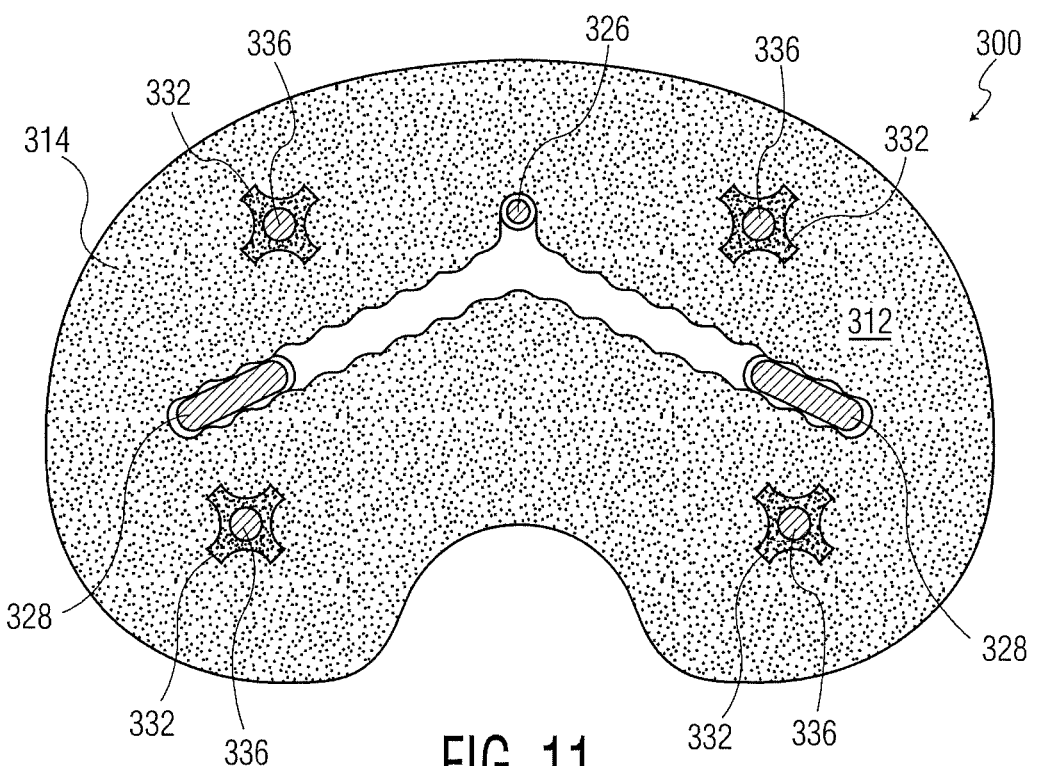
FIG. 11 shows a partial cross-sectional bottom view through lines 11-11 of FIG. 10.

Referring to FIG. 11, there is shown a cross-section along lines 11-11 looking up at the bottom surface 314 of the tibial component 300 of FIGS. 9 and 10 showing solid portions 326, 328 which connect keel 316 and struts to tibial baseplate 312. Spikes 330 are also shown with porous portions 332 and solid portions 336.

Figure 12:
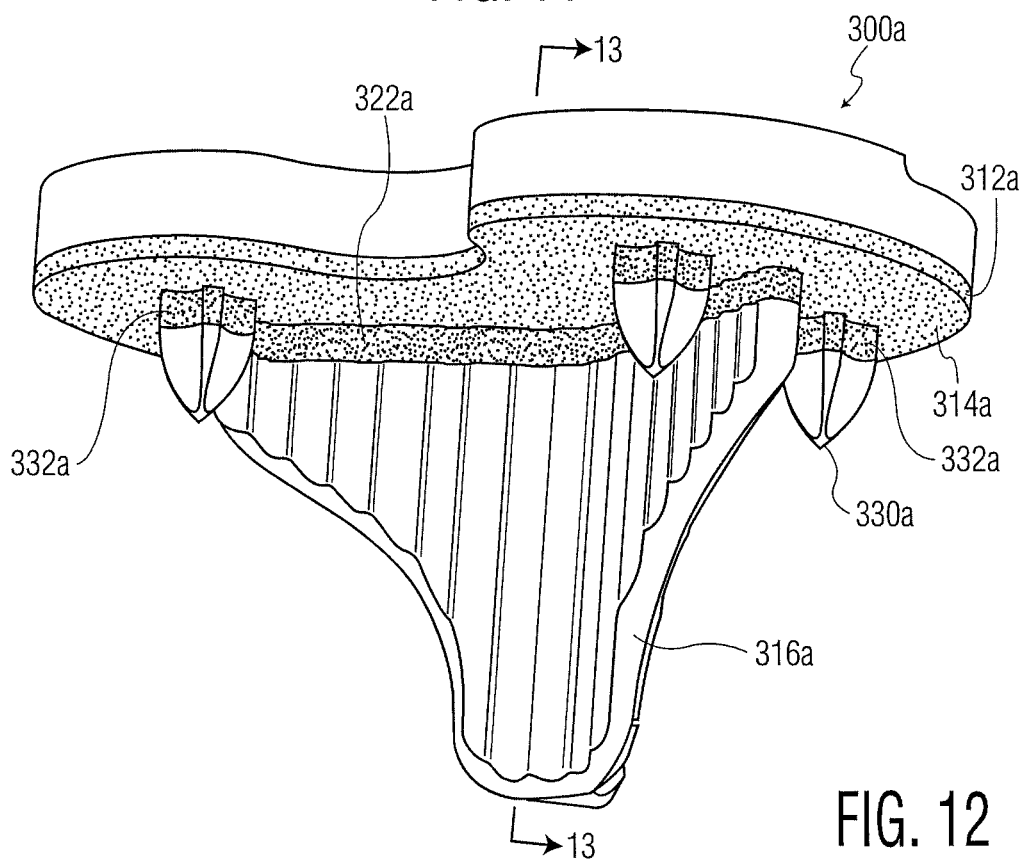
FIG. 12 is a perspective view of a tibial component similar to that shown in FIG. 9 with alternate design for the spikes.
Figure 13:
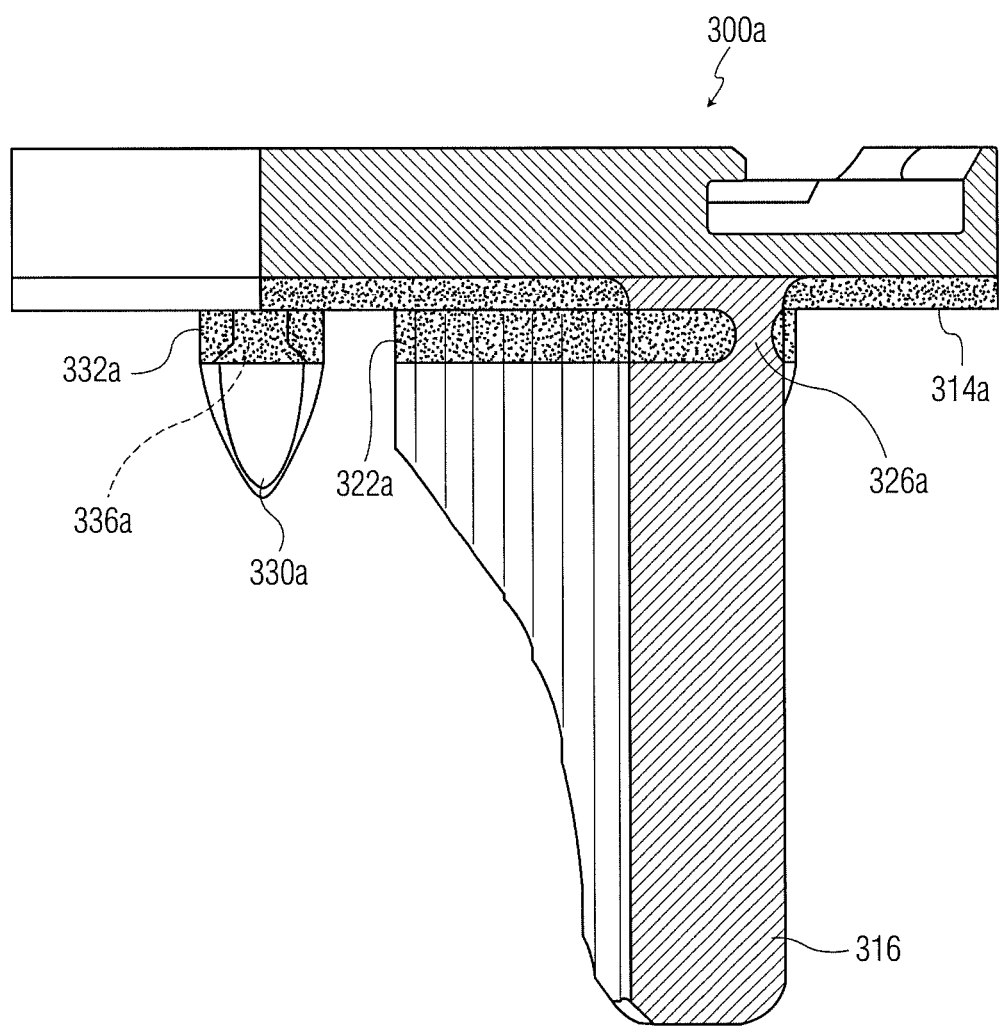
FIG. 13 is a cross-sectional through lines 13-13 of FIG. 12.
Figure 14:
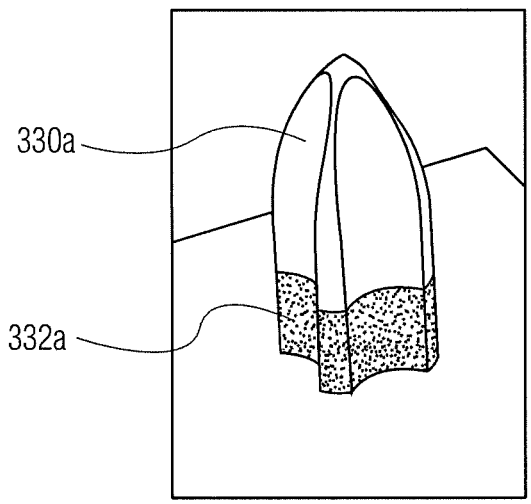
FIGS. 14-16 show alternate designs for the spikes used on the tibial component as shown in FIGS. 9-13.
Figure 15:
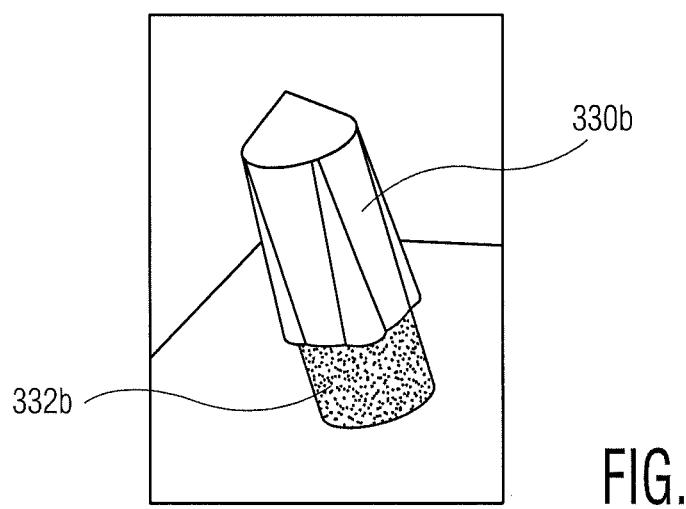
Figure 16:
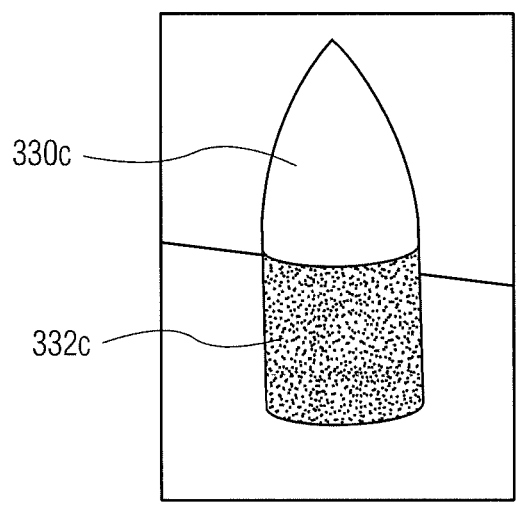

Referring to FIG. 12, there is shown an alternate embodiment 300a of tibial component 300. This embodiment is in all respects the same as 300 with the exception of the design of the spikes 330a, which have a cruciform shape. As can be seen, there are identical porous areas 332a on the v-shaped keel 316a and on areas 332a or spikes 330a. As seen in FIG. 13, spikes 330a have solid cores 336a surrounded by porous areas 332a. Also shown is solid central strut 326a surrounded by porous area 322a. The porous area 314a and 322a are also identical as those shown with regard to tibial component 300. These elements are shown in FIG. 13 in cross-section along lines 13-13 of FIG. 12. Various design spikes are shown in FIGS. 14-16 with FIG. 15 showing spikes similar to 330a and FIG. 16 showing spike 330b with FIG. 16 showing at an alternate spike design 330c. All the spikes include solid cores on porous areas 332a, b, c surrounding the cores.

Figure 17:
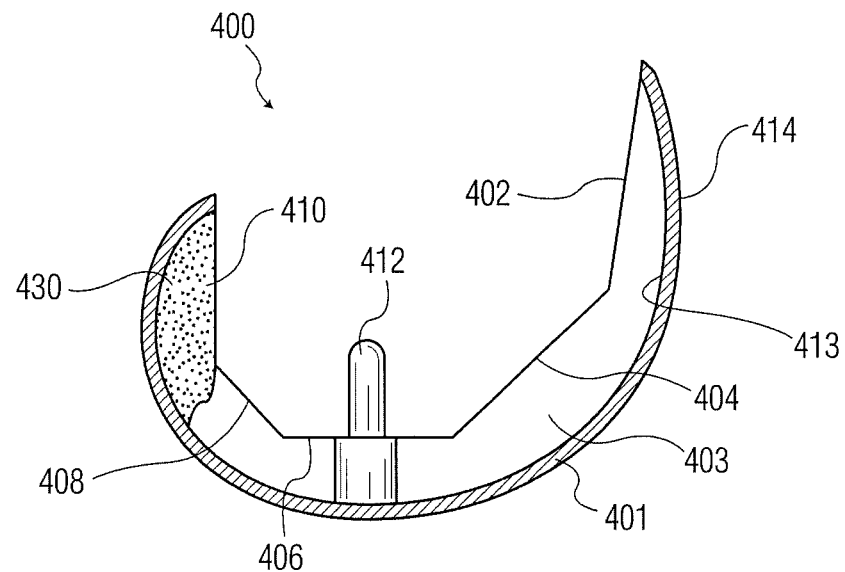
FIG. 17 is a cross-sectional view of a semi-hollow femoral component manufactured by the process described herein.
Figure 18:
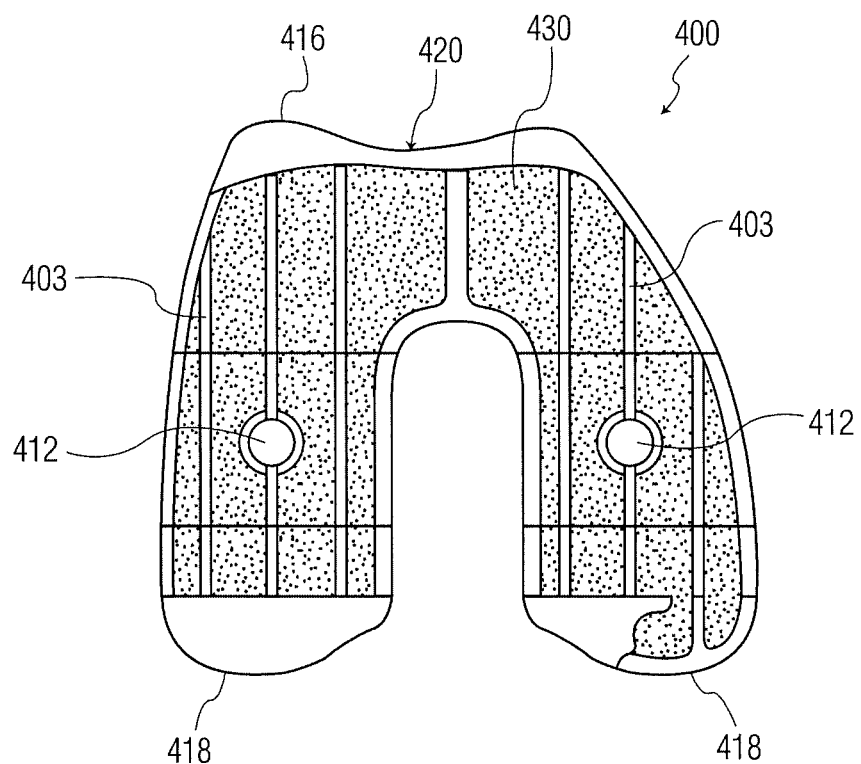
FIG. 18 is a plan view of a femoral component as shown in FIG. 17.
Figure 19:
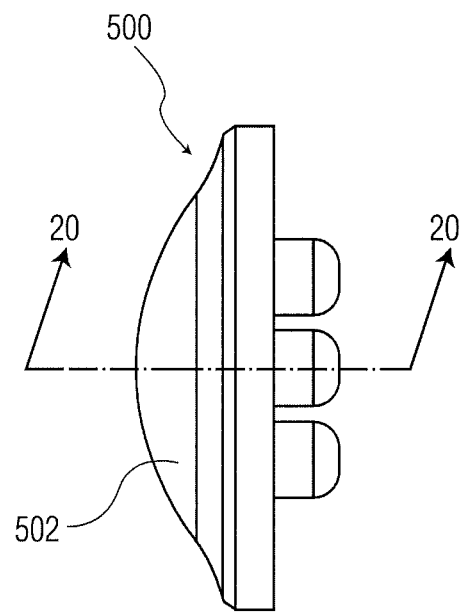
FIG. 19 shows a patella implant manufactured using the techniques described herein having a porous layer on either side of a fully dense layer and ultrahigh molecular weight polyethylene molded into one layer.
Figure 20:
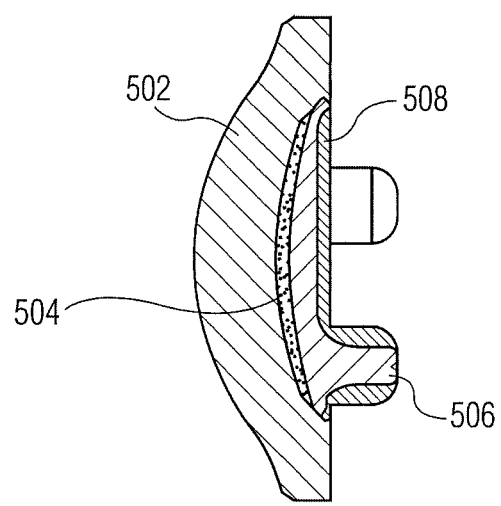
FIG. 20 is a cross-sectional view of the patella implant shown in FIG. 19 along lines 20-20.
Figure 21:
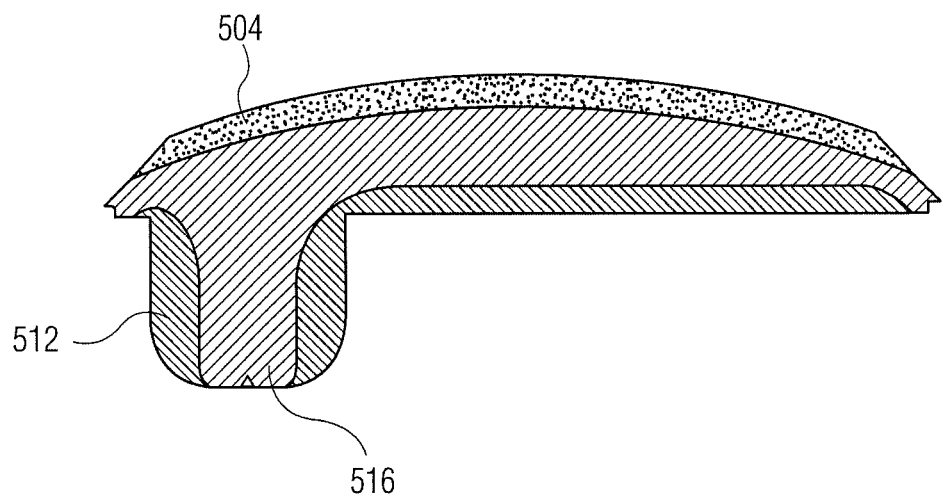
FIG. 21 shows the three layer metal backing of the patella component shown in FIGS. 19 and 20.

Referring to FIGS. 17 and 18, there is shown a semi-hollow femoral component generally denoted as 400 manufactured by the process described hereinbelow in which a thin solid articular element 401 is formed with an outer condylar bearing surface 414 followed by a plurality of solid plate-like reinforcing struts 402, forming a grid pattern and having outwardly facing surfaces 403, 404, 406, 408, and 410 matching the surface of a prepared femur (not shown). The femur is prepared in a well-known fashion to have distal, anterior, posterior, anterior chamfer, and posterior chamfer planar surfaces on which the prosthetic femoral component 400 is mounted. As shown in FIG. 17, the anterior inner surface 402 matches with the prepared planar femur anterior surface, surface 404 matches with the planar anterior chamfer surface, surface 406 matches with the planar distal surface of the femur, surface 408 matches with the planar posterior chamfer surface of the femur and surface 410 matches the prepared planar posterior surface of the femur. As indicated above, surfaces 402, 404, 406, 408, and 410 are formed by the end surface of spaced struts 403, which extend inwardly from an inner surface 413 of element 401 a distance sufficient to reinforce the thin articular element 401. As shown in FIGS. 17 and 18, a pair of pegs 412 extend proximally of distal surface 406 for insertion into blind bores formed in the distal surface of the prepared femur. The articulating surface 414 of element 401 of femoral component 400 is identical or similar to known solid femoral components. Surface 414 has a posterior condylar areas 418 and anterior condylar areas 416, including a recessed area 420 on which the patella (not shown) articulates. In the preferred embodiments, the areas between plate-like struts 403 are filled with a foam material 430, such as urethane foam, to further stiffen the femoral component. Plate-like outer bearing surface 401 may be hydroformed from sheet metal such as Titanium to have medial and lateral condyles on an intracondylar notch. The metal may be less than 0.125 inches thick.

Figure 22:
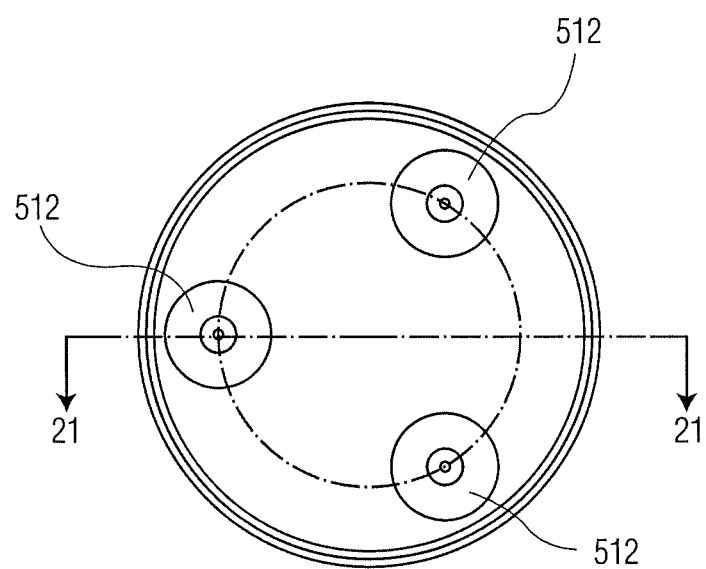
FIG. 22 is a bottom view of the patella component shown in FIGS. 19-21.

Referring to FIGS. 19-22, there is shown a patella generally denoted as 500, having a three-layer metal backing which is fabricated by the methods set forth below. Patella 500 includes a polyethylene bearing surface 502 mounted onto a first layer comprising a porous layer 504 of the patella 500, which layer 504 is formed on top of a solid or fully dense intermediate metal element 506, which in turn has a porous bone contacting layer 508 made of a second porous element formed thereon. Elements 504, 506, and 508 are formed by the selective laser melting (SLM) techniques set forth below in a single additive manufacturing operation. After the metal backing is formed, the polyethylene bearing element 502 is molded on porous layer 504. Solid or fully dense portion 506 gives the patellar implant structural integrity. Referring to FIG. 22, there is shown a bottom view in which three pegs 512 are shown which are adapted to engage bores in the prepared bone of the natural patella. Pegs 512 have solid cores 516 forming an integral part of fully dense or solid area 506. Cores 516 are surrounded by a porous metal area 508, which is adapted to allow bone tissue to grow therein. Porous area 504 is adapted to allow the infusion of the polyethylene bearing surface 502 as described in co-pending U.S. PCT Application PCT/US 2010/053314 (WO 2011/056422), the disclosure of which is incorporated herein by reference. The porous surface 504 may be convex to help form a convex UHMWPE bearing surface of the patella which typically engages the intracondylar area of the femoral implant.

The tibial component 10, 100, and 300 of the present invention as well as femoral component 400 and patella 500 are made at least in part by forming solid, porous and partially porous metallic structures. The method makes use of SLM laser technology by employing a variety of scanning strategies. Typical metal and metal alloys employed include stainless steel, cobalt chromium alloys, titanium and its alloys, tantalum and niobium, all of which have been used in medical device applications. This method can be used for medical device applications such as in the tibia where bone and soft tissue interlock with the tibial component is required, or where a controlled structure is required to more closely match the mechanical properties of the device with surrounding tissue.

The method produces a three-dimensional structure using a laser remelting process, for example, for building structures utilizing unit cells onto a premade solid tibial baseplate 12. When applied to a tibial component, the three-dimensional structure is used to provide porous spacer area 22 between the baseplate and a stem or keel 16. Keel 16 is preferably solid and is formed by the same laser remelting or fusion process as the porous spacer area 22. Thus a tibial component can be made by building porous spacer 22/solid keel 16 on premade baseplate 12 during a continuous operation to form a bone ingrowth structure and a solid keel or stem portion or a keel or stem with a solid surface and a porous core. The preferred materials used for both the baseplate and stem are titanium, cobalt chrome and tantalum but both stainless steel and niobium can also be used as well as any other suitable material. The tibial component 10 may be built from any of these materials, with the preferred material being titanium (Ti). The described method can be exploited on a commercial basis for the production of, for example, bone interlock surfaces on a device although it has many other uses.

According to the preferred method of forming a three-dimensional structure includes building the shape by laser melting powdered Ti and its alloys, stainless steel, cobalt chrome alloys, Ta or Nb using a continuous or pulsed laser beam. Individual layers of metal are scanned using a laser. Each layer or portion of a layer is scanned to create a portion of a plurality of predetermined unit cells, as will be described below. Successive layers are deposited onto previous layers and also may be scanned. The scanning and depositing of successive layers continues the building process of the predetermined unit cells. As disclosed herein, by continuing the building process refers not only to a continuation of a unit cell from a previous layer but also a beginning of a new unit cell as well as the completion of a unit cell.

The method can be performed so that the structure is either porous or solid and, if porous, the pores can be interconnecting to provide an interconnected porosity.

The method includes using a tibial baseplate of cobalt chrome alloy, titanium or alloy, stainless steel, niobium and tantalum, on which to build the porous layer of any one of the aforementioned metals and alloys by laser melting using a continuous or pulsed laser beam. Thus, a mixture of desired mixed materials can be employed.

The method includes a laser melting process which precludes the requirement for subsequent heat treatment of the structure, thereby preserving the initial mechanical properties of the baseplate metal. The equipment used for the manufacture of such a device could be one of many currently available including the MCP Realiszer, the EOS M270, Trumpf Trumaform 250, the Arcam EBM S12 and the like. The laser may also be a custom produced laboratory device.

The pore density, pore size and pore size distribution of the porous spacer area can be controlled (varied) from one location on the structure to another. It is important to note that successive powder layers can differ in porosity by varying factors used for laser scanning powder layers. Additionally, the porosity of successive layers of powder can be varied by either creating a specific type of unit cell or manipulating various dimensions of a given unit cell.

It will be appreciated that this method can, therefore, be used to produce article from the metals referred to which can be created to a desired shape and which may or may not require subsequent machining. Yet again, such an article can be produced so that it has a graded porosity of, e.g., non-porous through various degrees of porosity to the outer surface layer. Such articles could be surgical prostheses, parts or any other article to which this method of production would be advantageous.

To produce a porous spacer area structure, the nature of the material formed as a result of laser melting of powdered beads is principally dependent on the thermal profile involved (heating rate, soaking time, cooling rate); the condition of the raw material (size and size distribution of powder particles); and atmospheric conditions (reducing, inert or oxidizing chamber gas).

There have been a number of studies to determine the optimum pore structure for maximization of bone ingrowth on prostheses. The general findings suggest that optimum porosity is between approximately 20% and 40%, and aim to mid value with a mean volume percent of voids of about 70%. The preferred pore structure is interconnected, with a minimum pore size between about 80 µm and 100 µm and a maximum pore size between 80 µm and 800 µm. The structured thickness for ingrowth is 1.4-1.6 mm, but can be larger or smaller depending on the application.

In the present method the porous spacer structure is built in the form of a plurality of unit cells. Many designs of unit cells are possible to give the shape, type, degree, and size of porosity required. Such unit cell designs can be dodecahedral, octahedral, diamond, as well as many other various shapes. Additionally, besides regular geometric shapes as discussed above the unit cells of the present invention may be configured to have irregular shapes where various sides and dimensions have little if any repeating sequences. The unit cells can be configured to constructs that closely mimic the structure of trabecular bone for instance. Unit cells can be space filling, all the space within a three-dimensional object is filled with cells, or interconnected where there may be some space left between cells but the cells are connected together by their edges.

The cells can be distributed within the construct a number of ways. Firstly, they may be made into a block within a computer automated design system where the dimensions correspond to the extent of the solid geometry. This block can then be intersected with the geometry representing the component to produce a porous cellular representation of the geometry. Secondly, the cells may be deformed so as to drape over an object thus allowing the cells to follow the surface of the geometry. Thirdly, the cells can be populated through the geometry following the contours of any selected surface.

The unit cell can be open or complete at the surface of the construct to produce a desired effect. For instance, open cells with truncated lattice struts produce a surface with a porosity and impart the surface with some degree of barb.

Modifying the lattice strut dimensions can control the mechanical strength of the unit cell. This modification can be in a number of key areas. The lattice strut can be adjusted by careful selection of build parameters or specifically by changing the design of the cross-section of each strut. The density of the lattice can similarly be adjusted by modification of the density of the unit cells as can the extent and shape of porosity or a combination thereof. Clearly the overall design of the unit cell will also have a significant effect of the structural performance of the lattice. For instance, dodecahedral unit cells have a different mechanical performance when compared to a tetrahedral (diamond) structure.

The two key parameters used to define the relations regarding height, surface area, space height, volume of tetrahedron, and the dihedral angle of a tetrahedron are the strand length of the tetrahedron and, i.e., the diameter or height and width, cross section area of the strand, i.e., strut. These two parameters control the pore size and porosity of the structure. The parameter editor and relation editor within a typical CAD system can be used to control these parameters. Hence, by changing the parameters one can change the fundamental properties of the porous structure. The diamond or octahedral structure may have a circular cross-section strands or square cross-section strands.

A diamond or octahedral lattice structure can be made with and without laser beam compensation. Laser beam compensation essentially allows the diameter of the beam to be taken into account. Without it the constructed geometry is one beam diameter too wide as the beam traces out the contour of the particular section being grown. When laser beam compensation is utilized, the contour is offset half a beam diameter all around the constructed geometry which is represented in the CAD file. Although various parameters may be used, the parameters employed to create the porous ingrowth spacer include a laser power of 90-100 watts with an exposure time of 1,000 μsec from a point distance of about μm.

As shown in FIGS. 5A and 5B of U.S. Publication 2006/0147332, the preferred unit cell for the porous structures of the present invention may be constructed in the shape of a truncated octahedron. A truncated octahedron has eight regular hexagonal faces, six regular square faces, twenty-four vertices, and thirty-six edges. A square and two hexagons meet at each vertex. When the octahedron is truncated, it creates a square face replacing the vertex, and changes the triangular face to a hexagonal face. This solid contains six square faces and eight hexagonal faces. The square faces replace the vertices and thus this leads to the formation of the hexagonal faces. It should be noted here that these truncations are not regular polydra, but rather square-based prisms. All edges of an archamedian solid have the same length, since the features are regular polygons and the edges of a regular polygon have the same length. The neighbors of a polygon must have the same edge length, therefore also the neighbors and so on. As with previous unit cells, various dimensions such as the octahedron height, octahedron volume, octahedron surface area, octahedron dihydral angle, and truncated octahedron volume, truncated octahedron height, truncated octahedron area, truncated octahedron volume, truncated octahedron dihydral angle can be determined by simple trigonometry and are known by those skilled in the art.

In a method of use, a CAD model of the truncated octahedron is constructed using the sweep feature and calculations of between 10 and 1000 um and dimensions are incorporated using basic trigonometry. To tessellate the unit cell, the unit cell is first reoriented to enable easy tessellation and to reduce the number of horizontal struts in the model. Further, the model can be modified to remove all of the horizontal struts as shown in FIG. 7A of U.S. 2006/0147332. The modified structure is reproduced in order to save file size in the Steriolithography ("STL") format of the program. Next, in order to create the unit cells, the method of using a laser melting process is performed. In one preferred embodiment, the parameter chosen includes a laser power of 2260 watts for a bone ingrowth structure, 2512 watts for the solid structure an exposure of 410 and 200 μsec respectively with a focus distance of 1593 μm and, for the porous construct a point of distance of 65 μm. FIG. 7b of US 2006/0147332 illustrates a lattice structure formed using a plurality of individual truncated octahedron. The removal of various struts can create a barb effect on the exterior surface of the lattice structure.

EXAMPLE

The following is a method for making a partially porous implant and porous area by near-net shape building of a modular tibial tray component 10 of FIGS. 1-2 via additive (layer-by-layer) manufacturing.

A solid (non-porous) tray preform (e.g., forging) is partially or entirely machined to the final implant shape for example a tibial baseplate.

A layer-by-layer (additive manufacturing) direct build onto the solid tray preform 12 (e.g., Selective Laser Melting-SLM).

The construct is a hybrid SLM-built structure that is a combination of (a) porous SLM with a preferred porosity between 4-80% and a pore size in the range of 10 μm to 1000 μm, in which 100-400 μm is preferred for bone ingrowth and a "fully dense" SLM-built material that is less than 20% porous. This porous structure 22 is between 1 and 5 mm thick followed by a solid keel section 16. Both structures 16 and 22 may have a v-shape.

The SLM-built structure consists of a fully porous area 22 and a bone fixation keel 16, extending from the metaphyseal seating surface 14 of an orthopedic implant (such as tibial component 10) comprised of a porous portion adjacent to the metaphyseal porous seating surface and a fully dense portion extending to the diaphysis. Additionally, the fully dense keel portion 16 may be another hybrid structure where the center may be porous to reduce implant stiffness.

The SLM-built structure and the substrate the SLM-built structure is built onto are both integral parts of the implant. There is not removal of the SLM-built structure from the substrate (no EDM). That is, the fixturing for the additive manufacture process (SML) is part of the implant.

The SLM process uses only localized heating and, therefore, there is little to no affect from the heat on the underlying substrate mechanical properties. Further details of this manufacturing process are described in commonly owned U.S. patents and applications 2006/0147332, 2007/0142914, 2008/0004709, 2010/0010638, 2010/0291286, 2011/0014081, and U.S. Pat. No. 7,537,664, all the disclosures of which are incorporated herein by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A tibial implant comprising:
    a baseplate including a solid portion and a porous portion extending from the solid portion, wherein a first pore size at a first location of the porous portion is different than a second pore size at a second location of the porous portion;
    a keel extending from the baseplate and including a pair of flanges defining first and second planes intersecting along a keel axis; and
    a plurality of pegs extending from the baseplate to a point and having a cross-section formed by four free ends and four filets, each of the free ends being connected to two adjacent ones of the free ends by respective ones of the filets and having an edge surface,
    wherein the edge surfaces extend and narrow towards the point along corresponding ones of the free ends to define respective outer edges of the free ends, and
    wherein the edge surfaces of each of the free ends are convex and curve inwardly towards a central axis defined by the pegs.

2. The tibial implant of claim 1, wherein the plurality of pegs includes four pegs extending from the baseplate from locations spaced about the keel such that no three of the pegs are linearly aligned.

3. The tibial implant of claim 1, wherein an upper portion of the keel intersects the porous portion of the baseplate.

4. The tibial implant of claim 3, wherein the upper portion of the keel includes a porous section configured for being cut through with an implant removal tool.

5. The tibial implant of claim 1, wherein an upper portion of at least one of the pegs intersects the porous portion of the baseplate.

6. The tibial implant of claim 1, further comprising truncated struts on a portion of an exterior surface of the porous portion.

7. The tibial implant of claim 1, further comprising an additional flange extending from the intersection of the pair of flanges of the keel and from the baseplate, the additional flange extending along a third plane bisecting the first and the second planes.

8. The tibial implant of claim 1, wherein the porous portion includes edges defining polygons.

9. The tibial implant of claim 1, wherein the keel is integral with the baseplate to form a one-piece construct.

10. A tibial implant comprising:
   a solid bearing support portion;
   a porous bone-contacting portion extending from the bearing support portion, wherein a first pore size at a first location of the bone-contacting portion is different than a second pore size at a second location of the bone-contacting portion;
   a keel including three keel portions integral with and extending from the bone-contacting portion, the three keel portions intersecting at a common intersection; and
   a plurality of spikes extending from the baseplate in a same direction that the keel extends, each of the plurality of spikes extending to a point and having a cross-section formed by four free ends and four filets, each of the free ends being connected to two adjacent ones of the free ends by respective ones of the filets and having an edge surface,
   wherein the edge surfaces extend and narrow towards the point along corresponding ones of the free ends to define respective outer edges of the free ends,
   wherein the edge surfaces of each of the free ends are convex and curve inwardly towards a central axis defined by the spikes, and
   wherein each of the adjacent ones of the free ends is connected by respective ones of the filets.

11. The tibial implant of claim 10, wherein the plurality of spikes include four spikes extending from the baseplate from locations spaced about the keel such that no three of the spikes are linearly aligned.

12. The tibial implant of claim 10, wherein an upper portion of the keel intersects the bone-contacting portion of the baseplate.

13. The tibial implant of claim 12, wherein the upper portion of the keel includes a porous section configured for being cut through with an implant removal tool.

14. The tibial implant of claim 10, wherein an upper portion of at least one of the spikes intersects the bone-contacting portion of the baseplate.

15. The tibial implant of claim 10, further comprising truncated struts on a portion of an exterior surface of the bone-contacting portion.

16. The tibial implant of claim 10, wherein pores of the bone-contacting portion includes edges defining polygons.

17. A tibial implant comprising:
   a baseplate including a solid bearing support portion and a porous bone-contacting portion extending from the bearing support portion, wherein a first pore size at a first location of the bone-contacting portion is different than a second pore size at a second location of the bone-contacting portion;
   a keel including a pair of flanges integrally formed with the baseplate and defining planes intersecting along a keel axis and further including an additional flange integrally formed with the baseplate and extending from the intersection of the pair of flanges within a plane bisecting the pair of flanges; and
   four spikes extending from the baseplate from locations spaced about the keel and in a same direction that the keel extends, each of the spikes extending to a point and having a cross-section formed by four free ends and four filets, each of the free ends being connected to two adjacent ones of the free ends by respective ones of the filets and having an edge surface,
   wherein the edge surfaces extend and narrow towards the point along corresponding ones of the free ends to define outer edges of the free ends,
   wherein the edge surfaces of each of the free ends are convex and curve inwardly towards a central axis defined by the spikes, and
   wherein each of the adjacent ones of the free ends is connected by respective ones of the filets.

18. The tibial implant of claim 17, wherein an upper portion of the keel intersects the bone-contacting portion of the baseplate.

19. The tibial implant of claim 17, wherein a combination of the plurality of spikes, the keel, and the porous bone-contacting portion extend over an entirety of a profile of the solid bearing support portion.

20. The tibial implant of claim 17, wherein the keel extends through and from the bone-contacting portion.

* * * * *